United States Patent
Haroon et al.

(10) Patent No.: US 7,208,138 B2
(45) Date of Patent: Apr. 24, 2007

(54) CONTRAST ENHANCEMENT AGENT FOR MAGNETIC RESONANCE IMAGING

(75) Inventors: Zishan Haroon, Menlo Park, CA (US); Mark W. Dewhirst, Durham, NC (US); Charles S. Greenberg, Raleigh, NC (US); Michal Neeman, Mazkeret Batya (IL)

(73) Assignees: Duke University, Durham, NC (US); Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 11/294,625

(22) Filed: Dec. 5, 2005

(65) Prior Publication Data

US 2006/0083689 A1 Apr. 20, 2006

Related U.S. Application Data

(62) Division of application No. 10/025,698, filed on Dec. 18, 2001, now Pat. No. 6,972,122.

(60) Provisional application No. 60/260,377, filed on Jan. 5, 2001.

(51) Int. Cl.
*A61K 49/00* (2006.01)
*A61B 5/055* (2006.01)

(52) U.S. Cl. .................................. 424/9.1; 424/9.351
(58) Field of Classification Search ................ None
See application file for complete search history.

(56) References Cited

FOREIGN PATENT DOCUMENTS

| GB | WO 91/01144 | 2/1991 |
|----|----|----|
| WO | WO 89/00051 | 1/1989 |
| WO | WO 99/60018 | 11/1999 |
| WO | WO 9960018 A1 * | 11/1999 |
| WO | WO 99/61072 | 12/1999 |
| WO | WO 03/006070 | 1/2003 |

OTHER PUBLICATIONS

European Office Action dated May 9, 2006.

* cited by examiner

*Primary Examiner*—B. Dell Chism
(74) *Attorney, Agent, or Firm*—Jenkins, Wilson, Taylor & Hunt, P.A.

(57) ABSTRACT

Imaging agents for magnetic resonance imaging are disclosed. Methods of monitoring angiogenesis and the growth and remission of tumor tissue are also disclosed. Methods of monitoring blood clot formation and dissolution are additionally disclosed. Methods of monitoring wound healing are further disclosed. A kit for obtaining an image of a biological structure is further disclosed.

16 Claims, 4 Drawing Sheets

SEQUENCE LISTING

```
<160> NUMBER OF SEQ ID NOS: 3

<210> SEQ ID NO 1
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<223> OTHER INFORMATION: X is any amino acid

<400> SEQUENCE: 1

Asn Xaa Glu Gln Val Ser Pro
1               5

<210> SEQ ID NO 2
<211> LENGTH: 7
<212> TYPE: PRT
<213> ORGANISM: Homo sapiens

<400> SEQUENCE: 2

Asn Gln Glu Gln Val Ser Pro
1               5
```

```
<210> SEQ ID NO 3
<211> LENGTH: 7
<212> TYPE: PRT
<213> ORGANISM: Homo sapiens

<400> SEQUENCE: 3

Asn Gly Glu Gln Val Ser Pro
1               5
```

CONTRAST ENHANCEMENT AGENT FOR MAGNETIC RESONANCE IMAGING

RELATED APPLICATIONS

This application is a divisional patent application which claims the benefit of the filing date of U.S. Provisional Application Ser. No. 60/260,377, filed Jan. 5, 2001, and U.S. patent application Ser. No. 10/025,698, filed Dec. 18, 2001 now U.S. Pat. No. 6,972,122, the disclosure of which is incorporated herein by reference in its entirety.

TECHNICAL FIELD

The present invention relates to contrast enhancement agents for use in magnetic resonance ("MR") imaging and methods of non-invasively detecting and monitoring tumor angiogenesis, tumor growth and regression, wound healing and blood clot formation and dissolution.

Table of Abbreviations

AP alkaline phosphatase
CT computerized tomography
DMSO dimethylsulfoxide
DOTA 1,4,7,10-tetraazacyclododecane-1,4,7,10-tetraacetic acid
DTPA diethylenetriamine-pentaacetic acid
ECM extracellular matrix
EDTA ethylenediaminetetraacetic acid
ELISA enzyme linked immunoadsorbent assay
ESR electron spin resonance
fXIII factor XIII
fXIII$_a$ factor XIIIa
HRPO horseradish peroxidase
ICPAEC inductively coupled plasma atomic emission spectrometry
MR magnetic resonance
MRI magnetic resonance imaging
NMR nuclear magnetic resonance
PBS phosphate buffered saline
PET positron emission tomography
PI plasminogen inhibitor
PMSF phenylmethylsulfonyl fluoride
RARE rapid acquisition with refocused echoes
RF radio frequency
SNR signal-to-noise ratio
TBST Tris-buffered saline containing Tween
TCA trichloroacetic acid
TE echo time
TG tissue transglutaminase
TI time of inversion
$T_1$ spin lattice relaxation time
$T_2$ spin-spin relaxation time
VEGF vascular endothelial growth factor The standard two-letter abbreviations of elements referred to in the present invention are well known to those of the art and are not presented as a matter of convenience.

Amino Acid Abbreviations

| Single-Letter Code | Three-Letter Code | Name |
|---|---|---|
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

BACKGROUND ART

Medical diagnostic imaging has evolved as an important non-invasive tool for the evaluation of pathological and physiological processes. Presently, nuclear magnetic resonance imaging ("MRI") and computerized tomography ("CT") are two of the most widely used imaging modalities. Although both MRI and CT can be performed without the administration of contrast agents, the ability of many contrast enhancement agents to enhance the visualization of internal tissues and organs has resulted in their widespread use.

Principles of Magnetic Resonance Imaging and Contrast Enhancement Agents

Proton MRI is based on the principle that the concentration and relaxation characteristics of protons in tissues and organs can influence the intensity of a magnetic resonance image. Contrast enhancement agents that are useful for proton MRI effect a change in the relaxation characteristics of protons which can result in image enhancement and improved soft-tissue differentiation. Different classes of proton MR imaging agents include paramagnetic metal chelates and nitroxyl spin labeled compounds.

MRI is a diagnostic and research procedure that uses a large, high-strength magnet and radio-frequency signals to produce images. The most abundant molecular species in biological tissues is water. It is the quantum mechanical "spin" of the water proton nuclei that ultimately gives rise to the signal in all imaging experiments. In an MRI experiment, the sample to be imaged is placed in a strong static magnetic field (on the order of 1–12 Tesla) and the spins are excited with a pulse of radio frequency ("RF") radiation to produce a net magnetization in the sample. Various magnetic field gradients and other RF pulses then act on the spins to code spatial information into the recorded signals. The basic MRI experiment can be described, in one frame of reference, as follows. Pre-RF pulse spins can be thought of as collectively aligned along the Z-axis of a Cartesian coordinate system; application of one or a sequence of RF pulses "tip" the spins into the X-Y plane, from which position they will spontaneously relax back to the Z-axis. The relaxation of the spins is recorded as a function of time. Using this basic experiment, MRI is able to generate structural information in three dimensions in a relatively short period of time.

MR images are typically displayed on a gray scale with the color black representing the lowest measured intensity and white representing the highest measured intensity (I). This measured intensity is obtained by applying the formula I=C*M, where C is the concentration of spins (in an MRI experiment, this represents the water concentration) and M is a measure of the magnetization in the sample present at time of the measurement. Although variations in water concentration (C) can give rise to contrast in MR images, it is the strong dependence of the rate of change in the magnetization (M) on local environment that is the major source of variation in image intensity in an MRI experiment.

Two characteristic relaxation times are implicated in magnetic relaxation, the basis for MRI. $T_1$ is defined as the longitudinal relaxation time, and is also known as the spin lattice relaxation time ($1/T_1$ is a rate constant, $R_1$, the spin-lattice relaxation rate constant). $T_2$ is known as the transverse relaxation time, or spin-spin relaxation mechanism, which is one of several contributions to $T_2$ ($1/T_2$ is also a rate constant, $R_2$, the spin-spin relaxation rate constant). $T_1$ and $T_2$ have inverse and reciprocal effects on image intensity, with image intensity increasing either by shortening the $T_1$ or lengthening the $T_2$.

In order to increase the signal-to-noise ratio ("SNR"), a typical MR imaging scan (RF and gradient pulse sequence and data acquisition) is repeated at a certain rate for a predetermined number of times and the data is subsequently averaged. The signal amplitude recorded for any given scan is proportional to the number of spins that have decayed back to equilibrium in the time period between successive scans. Thus, regions with rapidly relaxing spins (i.e. those regions comprising spins having short $T_1$ values) will recover all of their signal amplitude between successive scans. The measured intensities of the regions with long T2 and short T1 will reflect the spin density, which correlates with the region's water content. Regions with long $T_1$ values, as compared to the time between scans, will progressively lose signal (i.e. the signal linewidth will broaden and "flatten out") until a steady state condition is reached. At the steady state condition, these regions will appear as darker regions in the final image. In extreme situations, the linewidth can be so large that the signal is indistinguishable from background noise.

Clinical MR imaging takes advantage of the fact that water relaxation characteristics vary from tissue to tissue, and this tissue-dependent relaxation effect provides image contrast, which in turn allows the identification of various distinct tissue types. Additionally, the MRI experiment can be set up so that regions of a sample with short $T_1$ values and/or long $T_2$ values are preferentially enhanced. Experiments so designed are known as $T_1$-weighted and $T_2$-weighted imaging protocols.

There is a rapidly growing body of literature demonstrating the clinical effectiveness of paramagnetic contrast agents. Paramagnetic contrast agents serve to modulate $T_1$ and/or $T_2$ values, and are typically designed with regard to a given metal nucleus, which is usually selected based on its effect on relaxation. The capacity to differentiate between regions or tissues that can be magnetically similar but histologically different is a major impetus for the preparation of these agents. Paramagnetic contrast agents provide additional image contrast, and thus enhanced images, of those areas where the contrast agent is localized. For example, contrast agents can be injected into the circulatory system and used to visualize vascular structures and abnormalities (See, e.g., U.S. Pat. No. 5,925,987), or even intracranially to visualize structures of the brain.

When designing contrast agents for use in MRI experiments, strict attention must be given to a variety of properties that will ultimately affect the physiological applicability of the agent, as well as the ability of the agent to provide contrast enhancement in an MRI image. Two fundamental properties that must be considered are a) biocompatibility, and b) proton relaxation enhancement. Biocompatability is influenced by several factors including toxicity, stability (thermodynamic and kinetic), pharmacokinetics and biodistribution. Proton relaxation enhancement and relaxivity is chiefly governed by the choice of metal employed in the agent, the rotational correlation times and the accessibility of the metal to surrounding water molecules, which permits the rapid exchange of metal-associated water molecules with the bulk solvent.

The measured relaxivity of the contrast agent is dominated by the selection of the metal atom. Paramagnetic metal ions, as a result of their unpaired electrons, act as potent relaxation enhancement agents. They decrease the $T_1$ relaxation times of nearby spins, exhibiting an $r^6$ dependency, where r is the distance between the two nuclei. Some paramagnetic ions decrease the $T_1$ without causing substantial linebroadening, for example gadolinium(III) ("Gd(III)"), while others induce drastic linebroadening, for example, superparamagnetic iron oxide. The mechanism of $T_1$ relaxation is generally a through-space dipole-dipole interaction between the unpaired electrons of a metal atom with an unpaired electron (the paramagnet) and those water molecules not coordinated to the metal atom that are in fast exchange with water molecules in the metal's inner coordination sphere.

The shortening of proton relaxation times by Gd(III) is mediated by dipole-dipole interactions between its unpaired electrons and adjacent water protons. The effectiveness of Gd(III)'s magnetic dipole drops off very rapidly as a function of its distance from these protons. Consequently, the protons which are relaxed most efficiently are those which are able to enter Gd(III)'s first or second coordination spheres during the interval between the RF pulse and signal detection. By way of example, regions associated with a Gd(III) ion having proximate water molecules appear bright in an MR image, while the normal aqueous solution appears as dark background when the time between successive scans in the experiment is short, for example in a $T_1$ weighted image.

Conversely, localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time ("TE") in a spin-echo pulse sequence experiment is long, for example in a $T_2$-weighted image.

The lanthanide atom Gd(III) has generally been chosen as the metal atom for contrast agents because it has a high magnetic moment ($\mu^2=63$ $BM^2$), a symmetric electronic ground state, $S^8$, and the largest paramagnetic dipole and the greatest paramagnetic relaxivity of any element. Gd(III) can be chelated with any of a number of substances to render the Gd(III) complex nontoxic, such as diethylenetriamine-pentaacetic acid ("DTPA"), 1,4,7,10-tetraazacyclododecane-1, 4,7,10-tetraacetic acid ("DOTA"), and derivatives thereof. See, U.S. Pat. Nos. 5,155,215; 5,087,440; 5,219,553; 5,188,816; 4,885,363; 5,358,704; 5,262,532; and Meyer et al., (1990) Invest. Radiol. 25:S53.

The stability constant (K) for the Gd-DTPA complex is very high (logK=22.4) and is more commonly known as the formation constant, expressed by the qualitative observation that the higher the value of logK, the more stable the complex. This thermodynamic parameter indicates that the fraction of Gd(III) ions that are in the unbound state will be quite small, and should not be confused with the rate (kinetic stability) at which the loss of metal occurs.

The water soluble chelate Gd-DTPA is stable, nontoxic, and one of the most widely used contrast enhancement agents in experimental and clinical imaging research. It was approved for clinical use in adult patients in June of 1988. Gd-DTPA is an extracellular agent that accumulates in tissue by perfusion-dominated processes. Image enhancements achieved using Gd-DTPA are well documented for a variety of applications including visualizing blood-brain barrier disruptions caused by space-occupying lesions and detection of abnormal vascularity. (Runge et al., (1991) *Magn, Reson. Imaging* 3:85; Russell et al., (1989) *Am. J. Roentgenol.* 152:813; and Meyer et al., (1990) *Invest Radiol* 25:S53). It has also been applied to the functional mapping of the human visual cortex by defining regional cerebral hemodynamics (Belliveau et al., (1991) *Science* 254: 719).

Another chelator used in Gd-based contrast agents is the macrocyclic ligand DOTA. The Gd-DOTA complex has been thoroughly studied in laboratory tests involving animals and humans. The complex is conformationally rigid, has an extremely high formation constant (logK=28.5) and, at physiological pH, possesses very slow dissociation kinetics. The Gd-DOTA complex was approved as an MRI contrast agent for use in adults and infants in France and has been administered to over 4,500 patients.

Tissue Transglutaminase

The extracellular matrix ("ECM") plays an important role in the regulation of tumor growth, metastasis and angiogenesis. To generate a new EC matrix, tumors are known to elicit wound-healing responses from the host tissues resulting in formation of granulation tissue at the advancing margins of the tumor. Tissue transglutaminase ("TG") is one of a family of crosslinking enzymes expressed in different forms in a variety of biological systems. TG is a calcium dependent enzyme that covalently crosslinks a wide variety of ECM proteins, producing a protease resistant matrix. TG is reported to be expressed at sites of wound healing and inflammation (Haroon et al., (1999a) *FASEB J.* 13:1787–95; Haroon et al., (1999b) *Lab. Invest.* 79:1679–86; Hettasch et al., (1996) *Lab. Invest.* 75:637–45) and, therefore, appears to play a role in the host response to these conditions. TG is also known to be expressed and active at sites of tumor progression.

TG catalyzes the formation of $\epsilon$-($\gamma$-glutamyl) lysine bonds (isopeptide bonds) between peptide bound glutamine residues and the primary amine group of various amines (Folk, (1983) *Adv. Enzymol. RAMB* 54: 1–56). These isopeptide bonds are stable and more resistant to proteolytic degradation than non-covalent linkages. The covalent crosslinking reaction increases the resistance of proteins to chemical, enzymatic and physical disruption (Greenberg et al., (1991) *FASEB J.* 5:3071–77). The list of proteins that are crosslinked by TG is extensive and includes extracellular adhesive proteins such as fibronectin, collagen, fibrinogen, fibrin, laminin/nidogen, osteoporin and vitronectin to name a few. See, Aeschlimann & Paulsson, (1991) *J. Biol. Chem.* 266:15308–17; Greenberg et al., (1987) *Blood* 70:702–9; Hohenadl et al., (1995) *J. Biol. Chem.* 270:23415–20; Sane et al., (1988) *Biochem. Biophys. Res. Commun.* 157:115–20. In addition to influencing matrix stability by producing stable crosslinks between matrix proteins, TG has been implicated in numerous other interactions to stabilize the ECM. TG has been shown to regulate the conversion of latent TGF $\beta$, a cytokine that can modify epithelial growth, enhance synthesis of various ECM proteins and inhibitors of metalloproteases (Clark & Coker, (1998) *Int. J. Biochem. Cell Biol.* 30: 293–98; Kojima et al., (1993) *J. Cell Biol.* 121: 439–48; Pepper, (1997) *Cytokine Growth Factor Rev.* 8: 21–43), to its active form. TG itself is induced by injury cytokines such as TNF$\alpha$, TGF$\beta$ and IL-6 (George et al., (1990) *J. Biol. Chem.* 265:11098–104; Ikura et al., (1994) *Biosci. Biotechnol. Biochem.* 58: 1540–41; Kuncio et al., (1998) *Am. J. Physiol.* 274: G240–45). The TG can also crosslink elafin and PAI-2, potent inhibitors of elastase and plasmin respectively, to ECM thus providing anti-protease capability to the matrix (Jensen et al., (1993) *Eur. J. Biochem.* 214:141–46; Nara et al., (1994) *J. Biochem.* (Tokyo) 115: 441–48). Fibroblasts transfected with TG have been shown to have a distinct spread morphology and increased resistance to protease digestion (Gentile et al., (1992) *J. Cell Biol.* 119: 463–74).

Plasma Factor XIII and fXIII$_a$

Plasma factor XIII (also known as fibrin stabilizing factor, fibrinoligase, or plasma transglutaminase) is a plasma glycoprotein that circulates in blood as a zymogen ($M_r \cong 320$ kD) complexed with fibrinogen (Greenberg & Shuman, (1982) *J. Biol. Chem.* 257: 6096–6101). The plasma factor XIII zymogen is a tetramer consisting of two a subunits ($M_r \cong 75$ kD) and two b subunits ($M_r \cong 80$ kD) (Chung et al., (1974) *J. Biol Chem.* 249: 940–50), having an overall structure designated as $a_2b_2$. The a subunit contains the catalytic site of the enzyme, while the b subunit is thought to stabilize the a subunit or to regulate the activation of factor XIII (Folk & Finlayson, (1977) *Adv. Prot. Chem.* 31: 1–133; Lorand et al., (1974) *Biochem. Biophys. Res. Comm.* 56: 914–922). The amino acid sequences of the a and b subunits are known (Ichinose et al., (1986a) *Biochem.* 25: 4633–38; Ichinose et al., (1986b) *Biochem.* 25: 6900–906). Plasma factor XIII occurs in placenta and platelets as an $a_2$ homodimer.

In vivo, activated factor XIII ("fXIII$_a$") catalyzes crosslinking reactions between other protein molecules. Factor XIII$_a$, a sister enzyme of tissue TG discussed above, catalyzes a number of covalent crosslinking reactions of fibrin in blood clots. These covalent fibrin crosslinking reactions render blood clots mechanically stable and greatly increase clot resistance to plasma degradation (fibrinolysis).

During the final stages of blood coagulation, thrombin converts the plasma factor XIII zymogen to an intermediate form (a'$_2$ b$_2$), which then dissociates in the presence of calcium ions to produce factor XIIIa, a homodimer of a' subunits. Placental factor XIII is also activated upon cleavage by thrombin. Factor XIIIa ("fXIII$_a$") is a transglutaminase that catalyzes the crosslinking of fibrin polymers through the formation of intermolecular $\xi$($\delta$-glutamyl) lysine bonds, thereby increasing clot strength (Chen & Doolittle, (1970) *Proc. Natl. Acad. Sci. U.S.A.* 66: 472–79; Pisano et al., (1972) *Ann. N.Y. Acad. Sci.* 202: 98–113). This crosslinking reaction requires the presence of calcium ions (Lorand et al., (1980) *Prog. Hemost. Throm.* 5: 245–290; Folk & Finlayson, (1977) *Adv. Prot. Chem.* 31: 1–133). Factor XIIIa also catalyzes the crosslinking of the $\delta$-chain of fibrin to $\alpha_2$-plasmin inhibitor and fibronectin, as well as the crosslinking of collagen and fibronectin, which might be related to wound healing (Sakata & Aoki, (1980) *J. Clin. Invest* 65: 290–97; Mosher, (1975) *J. Biol. Chem.* 250: 6614–21; Mosher & Chad, (1979) *J. Clin. Invest* 64: 781–787; Folk & Finlayson, (1977) *Adv. Prot. Chem.* 31:

1–133; Lorand et al., (1980) *Prog. Hemost. Throm.* 5: 245–90). The covalent incorporation of $\alpha_2$-plasmin inhibitor into the fibrin network might increase the resistance of the clot to lysis (Lorand et al., (1980) *Prog. Hemost. Throm.* 5: 245–90).

Simultaneous with catalyzing γ chain crosslinking, fXIII$_a$ catalyzes crosslinking of fibrin alpha ("α") chains to a plasminogen inhibitor, $\alpha_2$-PI. This $\alpha_2$-PI incorporation into a crosslinked clot gives a clot immediate protection against fibrinolysis. Subsequently, and at much slower rates (up to 6 days) in a clot, fXIII$_a$ catalyzes lateral crosslinking of a chains to form clusters of five to seven γ chains. In addition, fXIII$_a$ catalyzes (i) a chain crosslinking to γ dimers; and (ii) γ dimer crosslinking with other γ chains to form γ trimers and tetramers. In general, the older the clot is, the greater amount of the fibrin crosslinking is present and, consequently, the greater resistance the clot is to lysis.

Blood Clot Imaging

The ability to detect the presence of clots, and the ability to monitor their formation and dissolution, can eliminate a potentially life-threatening condition, particularly in a patient recovering from a myocardial infarction (heart attack). After a clot that has caused a myocardial infarction has been lysed, a second or third clot can reformat the same site, which can become more life-threatening than the formation of the first clot. This is because, when the first occluding clot is lysed, it is common that the clot does not entirely dissolve. As blood flow is restored over the undissolved portion of the clot, some blood constituents cause platelet deposition and promote further thrombosis. When this happens, the natural hemostatic balance (the balance between clot formation and clot degradation) is shifted from fibrinolysis toward thrombosis. The surface of any undissolved portion of the first clot is intrinsically thrombogenic, and more fibrin is often deposited before dissolution of the first clot is complete. This newly deposited fibrin gives the older, undissolved portion of the clot an enhanced opportunity to become more crosslinked. As a clot persists over time, more fibrin crosslinking occurs, and the clot becomes denser and more resistant to fibrinolysis, until a very mature, fibrin-dense clot is formed.

A patient suffering from a heart attack can be treated with agents to assist in restoring coronary blood flow. However, the patient still runs the risk of clot reformation and a subsequent occlusion of blood vessels. It is therefore desirable to monitor blood clot formation and dissolution in vivo. The ability to monitor the status of blood clots reduces the chance that a patient can suffer from the occurrence or re-occurrence of occluded blood vessels. A number of patents disclose the in vitro detection of blood clots (See. e.g., U.S. Pat. Nos. 6,022,747; 4,797,369) and the in vitro measurement of blood clot mass (See, e.g., U.S. Pat. No. 5,441,892). The in vivo detection of blood clots, however, has been elusive. In vivo detection of blood clots would be useful as a preventative measure, and would provide an in vivo a therapeutic and research tool for determining the effect of developed and candidate inhibitors of clot formation and effectors of clot dissolution.

Imaging Wound Healing

The ability to monitor and image internal wound healing is vital, yet has been elusive. In medical procedures wherein the wound healing process is not immediately observable, such as in a bowel resection or other surgical procedure, it is critical for the health care practitioner to be able to monitor the healing process. If such a wound is not healing properly, a potentially life-threatening condition can develop in a subject.

When a surgical procedure is performed on a structure that can be visually observed, an incision can easily be monitored for proper healing via visual inspection and other known methods, and there is no immediate need for forming an image of the wound healing structure. When an internal operation is performed, however, it is much more difficult to assess wound healing. Internal wounds, obviously, cannot be visually inspected. Techniques currently available to health care professionals for monitoring imagine internal wound healing are both limited and imprecise, or entirely unavailable. Additionally, known techniques cannot provide a detailed image of an internal wound healing structure.

Imaging Tumor Boundaries and Monitoring Tumor Growth and Remission

It is also important for a heath care practitioner to be able to identify the discrete boundaries of a tumor. Tumor growth and remission can be monitored by determining the size of the tumor, prior and subsequent to a treatment; the boundaries of the tumor can be used as an indicator of size. In a clinical setting, an observed reduction in tumor size can be indicative of the success of a particular treatment.

Associated with tumor growth, and a contributing factor to tumor size, is the phenomenon of angiogenesis. Under normal physiological conditions, humans or animals undergo angiogenesis only in very specific restricted situations. For example, angiogenesis is normally observed in wound healing, fetal and embryonal development and formation of the corpus luteum, endometrium and placenta. Uncontrolled angiogenesis is associated with tumor metastasis. Folkman, (1995) *New Engl. J. Med.* 28:333(26), 1757–63. Indeed, tumors have been loosely characterized in the art as wounds that do not heal. Dvorak et al., (1987) *Lab. Invest.* 57(6): 673–86.

Imaging Angiogenic Tissue

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, and abnormal growth by endothelial cells supports the pathological damage seen in these conditions. The diverse pathological disease states in which unregulated angiogenesis is present have been grouped together as angiogenic-dependent or angiogenic-associated diseases.

It is also recognized that angiogenesis plays a major role in the metastasis of a cancer. If this angiogenic activity could be repressed or eliminated, then the tumor, although present, would not grow. In lieu of modulating angiogenesis, it is desirable to observe tumor growth and size by monitoring angiogenesis, and conversely, to observe angiogenesis in a tumor by monitoring tumor growth and size. It can also be valuable to monitor angiogenesis in non-tumor tissues, and ideally, a system designed to monitor and/or image angiogenic tumor tissue will be equally applicable to monitor and/or image angiogenic non-tumor tissue.

Detection and monitoring of tumor growth and remission is vital for the effective diagnosis and treatment of cancer. Current methods for detecting tumor growth and regression using CT scan, positron emission tomography ("PET"), optical imaging and MRI are limited in their ability to distinguish between normal and tumor tissue. Additionally, the ability to image blood clot and their formation finds application in a variety of different scenarios. Blood clot imaging is presently limited by a variety of obstacles, one of which is the inability to selectively image blood clots over other tissues and structures. Further, there is no currently available method of monitoring internal wound healing, nor is there an adequate method of monitoring angiogenic activity in tumor and non-tumor tissue. What is needed, therefore, is a non-invasive method of monitoring tumor growth or regression, blood clot formation and dissolution, angiogenesis and wound healing in a subject that offers superior sensitivity, relative to the currently available methods.

DISCLOSURE OF THE INVENTION

A contrast enhancement agent useful for providing an image of a biological sample is disclosed. The agent comprises at least one peptide comprising the amino acid sequence NXEQVSP (SEQ ID NO: 1), wherein X is any amino acid, at least one paramagnetic metal ion and at least one chelator. Preferably, the paramagnetic metal ion is selected from the group consisting of transition and inner transition elements. More preferably, the paramagnetic metal ion is selected from the group consisting of Gd(III), Mn(II), Cu(II), Cr(III), Fe(II), Fe(III), Co(II), Er(II), Ni(II), Eu(III) and Dy(III). Even more preferably, the chelator is selected from the group consisting of DTPA, substituted DTPA, DOTA, substituted DOTA, EDTA, substituted EDTA, CDTA and substituted CDTA. Most preferably, the peptide comprises the amino acid sequence NQEQVSP (SEQ ID NO: 2) or NGEQVSP (SEQ ID NO: 3), the paramagnetic metal ion is gadolinium and the chelator is DTPA. A contrast enhancement agent of the present invention in lyophilized form is also disclosed.

A method for preparing a contrast enhancement agent is disclosed. The method comprises (a) preparing a lyophilized contrast enhancement agent; and (b) admixing the imaging agent with an aqueous pharmaceutically acceptable diluent, whereby a contrast enhancement agent is prepared. Preferably, the aqueous pharmaceutically acceptable diluent is phosphate buffer saline.

A method of non-invasively forming an image of a biological sample is disclosed. The method comprises (a) providing a contrast enhancement agent comprising at least one peptide comprising the sequence NXEQVSP (SEQ ID NO: 1), wherein X is any amino acid, at least one paramagnetic metal ion and at least one chelator; (b) introducing the imaging agent into a biological sample; and (c) scanning the biological sample using magnetic resonance imaging to form visible images of the biological sample, whereby an image of a biological sample is formed. Preferably, the paramagnetic metal ion is selected from the group consisting of transition, lanthanide and actinide elements. More preferably, the paramagnetic metal ion is selected from the group consisting of Gd(III), Mn(II), Cu(II), Cr(III), Fe(II), Fe(III), Co(II), Er(II), Ni(II), Eu(III) and Dy(III). Even more preferably, the chelator is selected from the group consisting of DTPA, substituted DTPA, DOTA, substituted DOTA, EDTA, substituted EDTA, CDTA and substituted CDTA. Most preferably, the peptide comprises the amino acid sequence NQEQVSP (SEQ ID NO: 2) or NGEQVSP (SEQ ID NO: 3), the paramagnetic metal ion is gadolinium and the chelator is DTPA. It is also preferable that the contrast enhancement agent is disposed in a pharmaceutically acceptable diluent and that the biological sample is disposed in a subject. Additionally, it is preferable that the subject is a mammal, particularly a human, cat, dog or mouse, and that the biological sample is tumor tissue, angiogenic tissue, wounded tissue, blood or a blood clot.

A kit for obtaining an image of a biological structure is disclosed. The kit comprises a two-vial system of a lyophilized imaging agent and an aqueous diluent, comprising (a) a first vial comprising lyophilized contrast enhancement agent; and (b) a second vial comprising a pharmaceutically acceptable diluent. Preferably the lyophilized contrast enhancement agent comprises gadolinium, DTPA and a peptide comprising the sequence NXEQVSP (SEQ ID NO: 1), wherein X is any amino acid, and the pharmaceutically acceptable diluent comprises phosphate buffered saline.

Some of the objects of the invention having been stated hereinabove, other objects will be evident as the description proceeds, when taken in connection with the accompanying drawings as best described hereinbelow.

DETAILED DESCRIPTION OF THE INVENTION

Figure 1A:
FIG. 1A is a photograph of tissue depicting TG expression at the border zones between normal and injured tissue. TG appears brown in the figure.

A contrast enhancement agent useful for providing an MR-based image of tumor boundary regions and blood clots is an aspect of the present invention. Notably, the formation (and the dissolution) of blood clots can be monitored in real time. The contrast enhancement agents of the present invention comprise at least one peptide comprising the amino acid sequence NXEQVSP (SEQ ID NO: 1), wherein X is any amino acid, at least one paramagnetic metal ion and at least one chelator. Most preferably, the peptide comprises the amino acid sequence NQEQVSP (SEQ ID NO: 2), the paramagnetic metal ion is gadolinium and the chelator is DTPA.

The present invention also discloses a method of non-invasively forming an image of a tumor boundary and allows real-time imaging of blood clot formation. These abilities are made possible by the contrast enhancement agents of the present invention. The method of generating an image comprises (a) providing a contrast enhancement agent comprising at least one peptide comprising the sequence NXEQVSP (SEQ ID NO: 1), wherein X is any amino acid, at least one paramagnetic metal ion and at least one chelator;

(b) introducing the imaging agent into a biological sample (for example, tumor tissue or a blood sample); and (c) scanning the biological sample using magnetic resonance imaging to form visible images of the biological sample. Most preferably, the peptide comprises the amino acid sequence NQEQVSP (SEQ ID NO: 2), the paramagnetic metal ion is gadolinium and the chelator is DTPA.

A key to the utility of the disclosed contrast enhancement agents is that they are recognized by TG, an enzyme that is found in high concentrations at the boundary between normal and tumor tissue, and in the tissue surrounding wounds. The disclosed contrast enhancement agents are also recognized by the enzyme fXIII$_a$, which is involved in the formation of blood clots. Thus, a contrast enhancement agent of the present invention is useful for generating highly detailed MR-based images of tumor and wound tissue, and for generating real-time images of blood clot formation and dissolution. In a clinical setting, the contrast enhancement agents of the present invention are particularly useful for monitoring tumor growth and remission. Additionally, the contrast enhancement agents of the present invention will be clinically applicable for monitoring blood clot formation and dissolution in patients whose health is threatened by blood clot formation. Moreover, the present invention is also useful as a research tool for determining the effect of candidate tumor treatment therapeutics and candidate blood clot modulating therapeutics.

I. Definitions

Following long-standing patent law convention, the terms "a" and "an" mean "one or more" when used in this application, including the claims.

As used herein, the term "angiogenesis" means the generation of new blood vessels into a tissue or organ. The term "angiogenesis" also specifically encompasses blood vessel growth in tumor tissues.

As used herein, the term "biological activity" means any observable effect flowing from interaction between a transglutaminase polypeptide and a ligand. Representative, but non-limiting, examples of biological activity in the context of the present invention include TG and fXIII$_a$ crosslinking ability. Representative ligands can comprise a peptide of the present invention, such as those presented in SEQ ID NO: 1.

As used herein, the term "candidate substance" means a substance that is believed to interact with another moiety, for example a given ligand that is believed to interact with a transglutaminase polypeptide, or fragment thereof, and which can be subsequently evaluated for such an interaction. Representative candidate compounds or substrates include xenobiotics such as drugs and other therapeutic agents, carcinogens and environmental pollutants, natural products and extracts, as well as endobiotics such as steroids, fatty acids and prostaglandins. Other examples of candidate substances that can be investigated using the methods of the present invention include, but are not restricted to, agonists and antagonists of a tissue transglutaminase polypeptide, agonists and antagonists of a factor XIII/plasma transglutaminase polypeptide, toxins and venoms, viral epitopes, hormones (e.g., opioid peptides, steroids, etc.), hormone receptors, peptides, enzymes, enzyme substrates, co-factors, lectins, sugars, oligonucleotides or nucleic acids, oligosaccharides, proteins, small molecules and monoclonal antibodies.

As used herein, the term "crosslink" means the joining of two entities by the formation of one or more covalent bonds.

As used herein, the term "detecting" means confirming the presence of a target entity by observing the occurrence of a detectable signal, such as a radiologic or spectroscopic signal that will appear exclusively in the presence of the target entity.

As used herein, the term "endothelium" means a thin layer of flat epithelial cells that lines serous cavities, lymph vessels, and blood vessels.

As used herein, the term "expression" generally refers to the cellular processes by which a biologically active peptide or polypeptide is produced from RNA.

As used herein, the term "hybridization" means the binding or crosslinking of a probe molecule, a molecule to which a detectable moiety has been bound, to a target sample.

As used herein, the term "inner transition elements" means those elements known as lanthanide (or rare earth) and actinide elements. Inner transition elements are also known as f-block transition elements.

As used herein, the term "isolated" means oligonucleotides substantially free of other nucleic acids, proteins, lipids, carbohydrates or other materials with which they can be associated, such association being either in cellular material or in a synthesis medium. The term can also be applied to peptides, in which case the peptide will be substantially free of nucleic acids, carbohydrates, lipids and other undesired peptides and polypeptides.

As used herein, the term "labeled" means the attachment of a moiety, capable of detection by spectroscopic, radiologic or other methods, to a probe molecule.

As used herein, the terms "metal chelator" and "chelator" are used interchangeably and mean a molecule that forms a stable complex with a traceable metal atom under physiological conditions in that the metal remains bound to the conjugate in vivo.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein, the term "modulate" means an increase, decrease, or other alteration of any or all chemical and biological activities or properties of a wild-type or mutant fXIII$_a$ or TG polypeptide.

As used herein, the term "mutant" means a peptide or polypeptide which is obtained by replacing at least one amino acid residue in a native peptide, polypeptide or nucleic acid sequence with a different amino acid residue or nucleic acid and/or by adding and/or deleting amino acid residues or nucleic acids.

For a peptide or polypeptide, the addition or deletion can be within the native peptide or polypeptide or at the N- and/or C-terminus of a peptide or polypeptide corresponding to a native peptide or polypeptide which has substantially the same three-dimensional structure as the native peptide or polypeptide from which it is derived. The phrase "having substantially the same three-dimensional structure" means having a set of atomic structure coordinates that have a root mean square deviation (RMS deviation) of less than or equal to about 1 Å when superimposed with the atomic structure coordinates of the native polypeptide from which the mutant is derived when at least about 50% to 100% of the $C_\alpha$ atoms of the native peptide polypeptide are included in the superposition.

As used herein, the term "mutation" carries its traditional connotation and means a change, inherited, naturally occurring or introduced, in a nucleic acid or peptide sequence, and is used in its sense as generally known to those of skill in the art.

As used herein, the term "sequencing" means determining the ordered linear sequence of nucleic acids or amino acids of a DNA or protein target sample, using conventional manual or automated laboratory techniques.

As used herein, the term "small molecule" means a molecule having a molecular weight between 5 and 10 kDa.

As used herein, the term "substantially pure" means that the polynucleotide, peptide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the terms "transglutaminase", and "TG" are used interchangeably and mean any member of the family of enzymes classified as EC 2.3.2.13, irrespective of the common name of the enzyme.

As used herein, the term "TG-recognized" means the ability to bind or be crosslinked by a transglutaminase enzyme. Due to their similar crosslinking profiles, the term also encompasses the ability to bind or be crosslinked by $fXIII_a$.

As used herein, the term "transition elements" means those elements found in columns IIIB, IVB, VB, VIIB, VIIIB IB and IIB of the Periodic Table of Elements. Transition elements are also known as d-block elements.

II. General Considerations

One aspect of the present invention involves magnetic resonance-based imaging techniques. The magnetic resonance imaging techniques employed in the present invention are known and are described, for example, in Kean & Smith, (1986) *Magnetic Resonance Imaging: Principles and Applications*, Williams and Wilkins, Baltimore, Md. Contemplated MRI techniques include, but are not limited to, nuclear magnetic resonance ("NMR") and electronic spin resonance ("ESR"). The preferred imaging modality is NMR.

Standard equipment, conditions and techniques can be used to generate images; appropriate equipment, conditions and techniques can be determined in the course of experimental design. When in vivo MRI experiments are performed in the context of the present invention, they will be performed on a suitable NMR spectrometer.

In another aspect of the present invention, a contrast enhancement agent can be introduced into a biological structure disposed in a subject. The mode of administration of a contrast enhancement agent of the invention to a sample or subject can determine the sites and/or cells in the organism to which an agent will be delivered. The contrast enhancement agents of the present invention will generally be administered in admixture with a pharmaceutical diluent selected with regard to the intended route of administration and standard pharmaceutical practice. The preparations can be injected into a subject parenterally, for example, intraarterially or intravenously. For parenteral administration, a preparation can be used, e.g., in the form of a sterile, aqueous solution; such a solution can contain other solutes, including, but not limited to, salts or glucose in quantities that will make the solution isotonic. In another aspect, a contrast enhancement agent can be injected directly into a tumor. In this aspect, the preparation will be injected in accordance with the above guidelines.

When a contrast enhancement agent of the present invention is administered to humans, the prescribing physician will ultimately determine the appropriate dosage for a given human subject, and this can be expected to vary according to the weight, age and response of the individual as well as the nature and severity of the patient's condition.

A further aspect of the present invention involves freeze drying, or lyophilizing, a contrast enhancement agent to dryness. A lyophilized contrast enhancement agent can be stored at 4° C. for long periods of time. Methods of lyophilizing and freeze drying samples are known in the art. See, e.g., Everse & Stolzenbach, (1971) *Methods Enzymol.*, 22: 33–39, Academic Press, New York; Flosdorf, (1949) *Freeze-Drying*, Rheinhold Publishing Corporation, New York. In preparing a kit of the present invention, it is desirable to lyophilize the contrast enhancement agent in the same vial in which it will be distributed. An aqueous solution of the contrast enhancement agent herein disclosed is added to the vial after filtering through a sterilizing filtration system, such as a 0.22 micron filter typically used in sterilizing proteins or peptides. The contents of each vial can then be lyophilized and afterwards the vials capped and sealed under sterile conditions. A sterile final product is desirable when the product is going to be used for parenteral administration. In general the most useful container for use as a vial are the glass bottles typically used for lyophilizing biological materials. Another suitable container is a two-compartment syringe, wherein one compartment contains the lyophilized imaging agent cake and the other compartment contains the aqueous diluent. After lyophilization is complete, the vacuum within the vials or ampules can be released by filling the system with an inert gas, stoppered in place using standard equipment and then crimp sealed. Such a method will ensure a sterile final product.

III. Transglutaminase Structure and Function

Transglutaminases form a large family of protein crosslinking enzymes. At least six transglutaminase gene products have been characterized in higher vertebrates on the basis of their primary structure (Aeschlimann & Paulsson, (1994) *Thromb. Haemostasis* 71: 402–15). Transglutaminases are expressed in a variety of biological systems, including plasma and tissue. Enzymes of this class (EC 2.3.2.13) catalyze the $Ca^{2+}$-dependent transferase reaction, which leads to the formation of an isopeptide bond between the γ-carboxamide group of a peptide-bound glutamine residue and various primary amines (Folk & Finlayson, (1977) *Adv. Protein Chem.* 31: 1–133; Lorand & Conrad, (1984) *Mol. Cell. Biochem.* 58: 9–35). Most commonly, γ-glutamyl-ε-lysine crosslinks are formed in or between proteins by reaction with the ε-amino group of lysine residues.

Analysis of the three-dimensional structure of the α-subunit of fXIII, a plasma transglutaminase, showed that transglutaminases contain a central core domain containing enzymatic activity, an N-terminal β-sandwich domain and two C-terminal β-barrel domains, which are presumably involved in regulation of enzyme activity and specificity (Yee et al., (1994) *Proc. Natl. Acad. Sci. U.S.A.* 91: 7296–300).

The catalytic core domain of transglutaminases is structurally related to the cysteine proteases and forms a similar catalytic triad, Cys-His-Asp, in the enzyme active site. This provides strong evidence for the transglutaminase crosslinking reaction being the reverse of the proteolytic cleavage reaction catalyzed by cysteine proteases (Yee et al., (1996) *Sem. Thromb. Haemostasis* 22: 377–84). Transglutaminases undergo a number of post-translational modifications such as phosphorylation, fatty acylation, and proteolytic cleavage which regulate their enzymatic activity and sub-cellular localization (Aeschlimann & Paulsson, (1994) *Thromb. Haemostasis* 71: 402–15).

Figure 1B:
FIG. 1B is a photograph of tissue depicting TG expression at the border zones between normal and tumor tissue. TG appears brown in the figure.

An important aspect of the present invention involves the localized expression of TG. As noted above and depicted in FIGS. 1A and 1B, TG expression is high at the boundary between wounded tissue and normal tissue. FIG. 1A depicts the high level of expression of TG, denoted by brown color in the figure, at the boundary between normal and wounded tissue. FIG. 1B depicts the expression of TG at the boundary between normal and tumor tissue. In FIG. 1B, areas of high TG concentration are denoted by brown coloring. The present invention advantageously uses these observations to effectively target a contrast enhancement agent useful in MR-based imaging to regions of high TG expression and activity, namely the boundary between tumor and normal tissues.

IV. Synthesis and Characterization of Candidate Contrast Enhancement Agents

Building upon what is known about the structural characteristics, amino acid sequence and crosslinking profile of tissue TG, the present invention discloses methods for the design, synthesis and evaluation of TG substrates for use in MR imaging. It is established that TG activity is increased in areas of undergoing angiogenesis, blood clot formation and tumors, as depicted in FIGS. 1A and 1B. Thus, areas exhibiting elevated TG activity can be visualized using MRI, if a contrast enhancement agent can be directed to these structures. A TG-recognized substrate can be labeled with a contrast enhancer and subsequently contacted with a sample containing TG. The substrate, when bound, will be localized in areas exhibiting high-TG concentrations. When the tissue is visualized using MR techniques, the presence of the bound contrast enhancement agent facilitates the generation of detailed images of tissues having a high concentration of tissue TG.

IV.A. Design and Preparation of a Candidate Contrast Enhancement Agent

Design and preparation of a candidate contrast enhancement agent is a multistep process. First, suitable component entities are selected. A suitable metal ion, a suitable chelator and a suitable peptide or matrix protein should all be selected. Suitable peptides and matrix proteins will comprise at least the consensus sequence NXEQVSP (SEQ ID NO: 1), where X is any amino acid. This consensus sequence is recognized and bound by at least the TG and fXIII$_a$ proteins. Thus, a contrast enhancement agent of the present invention will include a peptide or matrix protein moiety that comprises this consensus sequence.

Broadly, a contrast enhancement agent of the present invention is formed by coordinating a metal ion to a chelator to form a metal-chelator complex. Subsequently, the metal-chelator complex is associated with a substrate that is recognized or can be bound by TG or fXIII$_a$, and can be referred to as "the protein component" of the contrast enhancement agent. Selection of an appropriate protein or peptide component can be an initial step.

TG has the ability to enzymatically crosslink all major matrix proteins. This observation can be advantageously used to design candidate contrast enhancement agents for MR imaging. TG's broad spectrum of substrates allows any of the major matrix proteins to be a component of a contrast enhancement agent of the present invention, including but not limited to the matrix proteins fibronectin, collagen, fibrinogen, fibrin, laminin/nidogen, osteoporin and vitronectin. Selection of a suitable matrix protein for the protein component of a contrast enhancement agent of the present invention can be made based on the protein's ability to be crosslinked, protein purification concerns, or other criteria recognized or desired. For use in the present invention, the matrix protein fibrinogen is an especially preferred TG substrate.

Following selection of a suitable TG substrate for incorporation in a contrast enhancement agent of the present invention, a metal ion and a chelator are selected. This selection can be made based on any of a variety of criteria, including the relaxation profile of a metal ion, the expected tolerance of a subject for a chelator or other criteria. A variety of organic metal-chelator pairs are documented in the literature and can be used in the present invention, including gadolinium diethylenetriaminepentaacetic acid-bismethylamide ("Gd-DTPA-BMA"), gadolinium cyclohexyl-diaminotetraacetic acid ("Gd-CDTA"), and gadolinium tetraazacylododecane tetraacetic acid ("Gd-DOTA"). Several organic-based metal-chelator pairs are used as contrast enhancement agents and are commercially available, such as MAGNEVIST® (gadopentetate dimeglumine), available from Berlex, Wayne, N.J., and PROHANCE® (gadoteridol), available from Squibb Diagnostics, Princeton, N.J.

When designing a contrast enhancement agent of the present invention, it is important to select an appropriate metal ion around which the organic component is coordinated. Appropriate metal ions for use in the present invention include, but are not limited to, the transition, lanthanide and actinide elements. Preferably, the metal ion is selected from the group consisting of Gd(III), Mn(II), Cu(II), Cr(III), Fe(II), Fe(III), Co(II), Er(II), Ni(II), Eu(III) and Dy(III), with Gd(III) especially preferred.

A variety of chelators useful in the present invention are also available. Of course the primary criteria in selecting a chelator for use in the present invention will be the ability of the chelator to coordinate a metal ion. Toxicity is also a primary concern. Suitable chelators include, but are not limited to, diethylenetriamine-pentaacetic acid (DTPA) and 1,4,7,10-tetraazacyclododecane-1,4,7,10-tetraacetic acid (DOTA). Ethylenediaminetetraacetic acid ("EDTA") and cyclic dietheylene triamine pentaacetic acid ("cDTPA") can also be used.

Following selection of appropriate metal and chelator entities, a metal-chelator complex ("MC complex") is formed. The complex can be formed by incubating a metal salt with a chelator, which can be added as a salt itself, using a variety of techniques.

A selected matrix protein is then complexed with a metal-chelator complex to form a matrix protein-metal-chelator complex ("MP-MC complex"). It is noted that the term "MP-MC complex" is a descriptive term and can function to distinguish the following matrix protein-based contrast enhancement agent synthesis from peptide-based contrast enhancement agent synthesis. Both matrix protein based- and peptide based-syntheses generate functional contrast enhancement agents covered by the present invention. Thus, an "MP-MC complex" means a functional contrast enhancement agent, regardless of whether a peptide, matrix protein, or a fragment thereof forms the protein component of the contrast enhancement agent. Different terminology is employed simply to differentiate and clarify the synthetic processes.

Although an MP-MC complex can be generated in many ways, it is preferable to generate the MP-MC complex by a modification of the method of Ogan et al. (Ogan et al., (1987) *Invest. Radiol.* 22:665–71), as follows. Matrix protein tagged with rhodamine (fibrinogen tagged with rhodamine is available from Molecular Probes, Inc., Eugene, Oreg.) is dissolved in 75 ml of 0.1 M sodium bicarbonate. 125 mg of N-hydroxysuccinimidobiotin (Sigma, St. Louis, Mo.) is dissolved in 12 ml of dry dimethyl formamide and added to the albumin while stirring for one hour on ice, followed by an additional two hours at room temperature. The product is dialyzed in HEPES buffer (pH=8.8) and is reacted with 5 g of cyclic dietheylene triamine pentaacetic acid anhydride (cDTPAa) (Sigma, St. Louis, Mo.) suspended in 25 ml DMSO at room temperature. cDTPAa is added in portions and the pH is adjusted immediately to 8.5 with 5N NaOH following each addition. The reaction mixture is stirred for two hours at 4° C. and extensively dialyzed against cold 0.1 M citrate buffer (pH=6.5). Metal is then added gradually, (for example 2.5 g of gadolinium(III) chloride ($GdCl_3$) (Sigma, St. Louis, Mo.) in 25 ml 0.1 sodium acetate buffer (pH=6.0)) and the mixture is stirred for 24 hours at 4° C. The product, an MP-MC complex, is extensively dialyzed against cold citrate buffer and then against distilled water. The product is lyophilized and the resulting powder stored at 4° C. and reconstituted to working concentrations in phosphate buffer saline. The MP-MC complex can be reconstituted and used as a contrast enhancement agent.

The above procedure for forming an MP-MC complex can be carried out with varied concentrations of reagents. In this fashion, optimal conditions for association of the protein component of a contrast enhancement agent with a desired MC complex can be determined.

IV.B. Synthesis and Evaluation of Candidate Low Molecular Weight Peptide-based Contrast Enhancement Agents It is known that one functional substrate for TG crosslinking comprises a sequence of seven amino acids, NXEQVSP (SEQ ID NO: 1), where X is the amino acid glutamine. This sequence is found in matrix proteins which TG is known to crosslink. Sakivama et al., *FASEB* (1999) 13:2214–24. Thus, a contrast enhancement agent of the present invention can comprise fewer amino acids than an entire matrix protein, as long as the protein component comprises SEQ ID NO: 1. Indeed, TG and $fXIII_a$-recognized peptides comprising SEQ ID NO: 1 are an aspect of the contrast enhancement agents of the present invention.

Peptides that are recognized by TG can be isolated from a biological sample or synthesized in the laboratory. Preferably, a peptide-based contrast enhancement agent of the present invention will have the specific amino acid sequence NQEQVSP (SEQ ID NO: 2), which is recognized by TG (See FIGS. 1A and 1B) and $fXIII_a$. Such peptides can subsequently be associated with an MC complex, which will be selected and prepared using the guidelines in Section IV.A. above. The MC complex Gd-DTPA is preferred for use in the present invention based on its established and well-documented properties; Gd-DTPA is widely recognized as a useful and consistent MRI contrast enhancement agent.

To complete the preparation of peptide-based TG and $fXIII_a$-specific contrast enhancement agents, an MC complex is associated with a protein component. The MC complex is prepared and associated with an appropriate protein component using the procedure presented in Section IV.A above. The concentration of metal chelated to the peptide is then determined, using the techniques described in Section IV.A. above.

The specificity of TG and $fXIII_a$ for SEQ ID NO: 2 assures the recognition of contrast enhancement agents comprising SEQ ID NO: 2 by TG and $fXIII_a$. Together, the Gd-DTPA-peptide moiety comprises a structure which is capable of recognition with a high degree of specificity by TG and $fXIII_a$, and which is capable of detection and imaging using known MR techniques. Thus, the peptide-based contrast enhancement agents of the present invention have utility as aids for the visualization of the structures, regions and tissues expressing TG, including the boundary regions of TG-containing tumors and forming blood clots.

IV.B.I. Generation of Peptides

The peptides of the present invention can be synthesized using standard methodology. In one embodiment, the peptides are synthesized on a solid amide resin using an automated peptide synthesizer using standard 9-fluorenyl-methyloxycarbonyl chemistry. See, Fields & Noble, (1990) *Int. J. Pept. Prot. Res.* 35: 161–214. Peptides of the present invention will contain the TG and $fXIII_a$ crosslinking motif, NXEQVSP (SEQ ID NO: 1), where X is the amino acid glutamine, positioned at the N-terminus, relative to the remainder of the peptide. Additionally, the peptides can contain a lysine tail of one to ten lysine residues positioned at the C-terminus of the peptide, relative to the TG crosslinking motif.

A moiety capable of fluorescence can be added to the extreme N-terminus of the generated peptide. The inclusion of a fluorescent moiety facilitates the easy detection of generated peptides and can assist in determining the degree to which a candidate contrast enhancement agent is crosslinked by TG or $fXIII_a$. In a preferred embodiment, the fluorescent moiety is α-dansyl-leucine group.

Additionally, the present invention encompasses peptide-based contrast enhancement agents wherein the residue at position 2 of the sequence NXEQVSP (SEQ ID NO: 1), where X is any amino acid, is a glycine residue. This inclusion of glycine at position 2 (SEQ ID NO: 3) produces an inert peptide with respect to TG and $fXIII_a$ crosslinking, and is useful as a control peptide in crosslinking assays. Peptides containing a glycine residue at position 2 can optionally contain one to ten residue lysine tails.

IV.C. Determining TG and fXIIIa Crosslinking Ability for a Candidate Contrast Enhancement Agent The degree to which a complex is crosslinked can be determined, using the generated MP-MC complex as the TG or $fXIII_a$ substrate, in order to assess the viability of the complex as a contrast enhancement agent. Inclusion of a fluorescent moiety in the synthesis of a contrast enhancement agent of the present invention enables an additional method by which a determination of a degree of crosslinking can be made. A degree of crosslinking can be determined by using a variety of assays, including those disclosed herein. See. e.g., Bäumert & Fasold, (1989) *Meth. Enzymol.* 172: 584, Academic Press, New York.

In one crosslinking assay, candidate MP-MC complexes are derivatized by adding a dansyl group to the N-terminus of the peptide component of the complex. Derivatization can be accomplished by synthesizing the peptide component of the complex so as to position a dansyl-containing residue at the N-terminus of the peptide, for example a dansyl leucine group. Dansyl groups are inherently fluorescent and therefore are well-suited to fluorescent detection of TG and $fXII_a$-catalyzed crosslinked structures.

TG or $fXIII_a$ is then incubated with the dansyl-derivatized peptide component under conditions conducive to the crosslinking reaction. Unbound ligand is removed and crosslink formation is detected. A candidate complex crosslinked by TG or $fXIII_a$ can be identified by the presence of a fluorescent signal.

Variations on the abovedescribed assay parameters are possible and will be apparent to one of skill in the art. For example, other fluorescent moieties can be used to label the protein component of a complex. Alternatively, the conditions of the crosslinking reaction can be adjusted. Finally, candidate complexes can be bound to a support; indeed, different candidate complex species can be bound to a support and screened at the same time. Thus, methods of high throughput assays to determine crosslinking of one or more candidate complexes are contemplated as an aspect of the present invention.

IV.D. Determining the Metal Content of a Candidate Contrast Enhancement Agent

Following preparation of a candidate contrast enhancement agent (the MP-MC complex), the number of bound metal atoms can be determined. The number of bound metal atoms serves as an indication of the degree of association of the MC complex with a protein or peptide component. The degree of association can be determined in the following manner, regardless of whether a candidate contrast enhancement agent is peptide- or matrix protein-based.

The quantity of peptide or protein in a candidate contrast enhancement agent in a sample is determined by UV absorbance of the sample at 280 nm against absorbance at 325 nm. After digestion of the sample in nitric acid, the number of metal chelates bound to the matrix protein is determined in a sample solution at appropriate wavelengths by inductively coupled plasma atomic emission spectrometry ("ICPAEC"). When the metal is gadolinium, appropriate wavelengths include 342.246 nm and 336.226 nm. Suitable instrumentation for plasma atomic emission spectrometry is commercially available and includes the SPECTROFLAME™ model (available from Spectro, Kieve, Germany). The metal concentration is determined by comparison of spectra with known standards, including solutions of metal halides. When the metal is gadolinium, suitable standards include $GdCl_3$, MAGNEVIST® (gadopentetate dimeglumine) and PROHANCE® (gadoteridol).

IV.E. Advantages of the Disclosed Contrast Enhancement Agents

The contrast enhancement agents of the present invention offer several advantages over currently known larger, high molecular weight plasma protein-based agents. An advantage of the smaller contrast enhancement agents of the present invention over larger entities is the minimization of an immune response mounted by a subject against the contrast enhancement agent. The smaller agents of the present invention can be more easily tolerated by a subject's immune system, and therefore the agents can find utility as agents for imaging structures in a subject having a hypersensitive immune response. See e.g., Kalka Moll, (2000) *J. Immunol.*, 164(2): 719–24.

Another advantage of the small peptide agents of the present invention over larger contrast enhancement agents is that the smaller agents of the present invention provide longer in vivo bioavailability of the agent throughout the tissues of a subject. This advantage is achieved by virtue of the small size of the agents, and consequently, the decreased immune response associated with the introduction of a contrast enhancement agent. The decreased immune response is achieved, at least in part, by virtue of the fact that smaller molecules are cleared more rapidly from the systems of a subject. The decreased immune response leads to less in vivo degradation of the agent, prior to crosslinking catalyzed by TG, and consequently a greater effective concentration of the agent at the border of a tumor. A greater effective concentration of the agent can facilitate images with a higher degree of detail.

Due to its low molecular weight, conjugated Gd-DTPA is cleared very rapidly from the bloodstream (½ in 20 minutes), and also from tissue lesions (tumors). See, Weinman et al., (1984) *Am. J. Roentgen.* 142: 619–24. Thus, another advantage of the small peptide agents of the present invention over larger contrast enhancement agents is the rapid systemic clearance of any unbound agent. High molecular weight contrast enhancement agents that are not bound to a specific structure can circulate through the systems of the body until they are ultimately cleared. This can generate unwanted immune responses and contribute to other deleterious effects. The small peptide agents of the present invention avoid these problems because of their small size, which makes them easier for a subject's body to clear.

V. Activity Assays

In another aspect of the present invention, the activity of TG and $fXIII_a$ can be assessed, when a candidate contrast enhancement agent of the present invention is presented as an enzyme substrate. It is desirable to determine TG and $fXIII_a$ activity as an additional gauge of the viability of a candidate agent. If the activity assay is performed in a multicomponent system, the secondary effects arising from the crosslinking of a candidate agent can also be assessed. Thus, activity assays can function as an additional indication of the viability of a candidate agent as an in vivo tool for generating detailed images.

V.A. Analysis of TG Activity

A determination of TG activity can be indicative of a candidate contrast enhancement agent's utility in vivo. For example, TG activity can be measured in the presence of a candidate contrast enhancement agent and compared to TG activity in a sample that contains a known TG substrate. TG activity can be measured as a function of a number of detectable phenomena, with preferred detection being achieved through fluorescent detection of crosslink formation. TG activity can be determined using activity assays as disclosed herein. Additional assays appropriate for use in the context of the present invention include those disclosed in Achyuthan, (1994) *Anal. Biochem.* 219:43–48.

Generally, fluorescence-based assays can be employed to determine the crosslinking ability of TG under a given set of conditions. TG crosslinking assays can be performed as follows. Candidate MP-MC complexes are derivatized by adding a dansyl or other fluorescent moiety-containing group, which is preferably an inherently fluorescent group such as dansyl leucine, to the N-terminus of the peptide component of the complex. TG is then incubated with the derivatized peptide component under conditions conducive to the crosslinking reaction. Unbound ligand is removed and crosslink formation is detected. A candidate complex crosslinked by TG can be identified by the presence of a fluorescent signal.

V.A.1. ELISA-based TG Activity Assays

Other methods of monitoring TG and $fXIII_a$-mediated crosslinking of a candidate contrast enhancement agent include fluorescence and radiolabel-based assays. These assays, and modifications to these assays, will become apparent in the course of experimental design. Desirable assays will allow a quantitative assessment, in addition to a qualitative assessment of pertinent kinetic parameters, such as the binding constant for the interaction between TG or $fXIII_a$.

An ELISA-based TG assay useful in the present invention is the following. TG activity is quantitated as a function of the incorporation of a biotin-labeled amine (in a preferred embodiment, N-(5'-aminopentyl)biotinamide is used) into a contrast enhancement agent of the present invention, which is bound to an immunoplate. The TG activity is then revealed by addition of streptavidin conjugated with alkaline phosphatase ("AP") or horseradish peroxidase ("HRPO"). See, Slaughter et al., (1992) *Anal. Biochem.* 205: 166–71. The assay is performed as follows.

Initially, welled plates are coated with substrate by adding a candidate contrast enhancement agent (maintained in phosphate buffered saline ("PBS") or $NaHCO_3$) to each well. The plates are incubated at 4° C. overnight or at 37° C. for 1 hour, and washed with PBS. 200 µl/well of 2% milk in PBS is added to block free protein-binding sites. The plates are again incubated for 1 hour at 37° C. Finally, the plates are washed three times with PBS. The washed plates can be stored at −20° C.

Next, a 10× reaction mixture is prepared, comprising 1M Tris HCl, pH=8.3; 50 mM $CaCl_2$; 1.5 M NaCl. Samples are prepared by adding the appropriate amount of 10× reaction mixture and 100 mM DTT to 1–10 µg/well purified TG, in anticipation of a final reaction volume of 200 µl. N-(5'-aminopentyl)biotinamide is added to a final concentration of 0.5 mM. The final volume of the samples is adjusted to 200 µl with water.

At this point, each sample will have a final volume of 200 µl and the following composition: 0.1 M Tris HCl, pH=8.5; 5 mM $CaCl_2$; 0.15 M NaCl; 5 mM DTT, which is added just before the incubation; 0.5 mM biotin labeled amine; and 1–10 µg of purified TG.

Negative controls are prepared by replacing TG with extraction buffer. The sample mixtures are added and the plate is incubated at 37° C. for 1 hour. After the 1-hour incubation, the plate is subsequently washed several times with TBST solution (10 mM Tris-HCl, pH=8.0, 150 mM NaCl, 0.05% Tween). 1–2 mg/ml streptavidin is diluted in TBST supplemented with 2% milk, and 200 µl is added per well. The plate is then incubated for 1 hour at room temperature. Finally, the plate is washed at least five times with TBST solution.

The reaction is developed by adding 200 µl of the appropriate substrate (Substrate 104 for AP-labeled streptavidin and POD Substrate for HRPO-labeled streptavidin). The plate is read at 405 nm when Substrate 104 is used, and at 495 nm when the POD Substrate is used.

TG activity is determined by comparing the absorbance values per min at the addition of substrate and after 30 min, after subtract the readings of the negative controls. Since differences in readings can vary as much as 0.1 OD, each measurement should be repeated, and the collection of measurements averaged to obtain an activity measurement.

V.B. $FXIII_a$ Mediated Crosslinking Assays

Figure 1C:
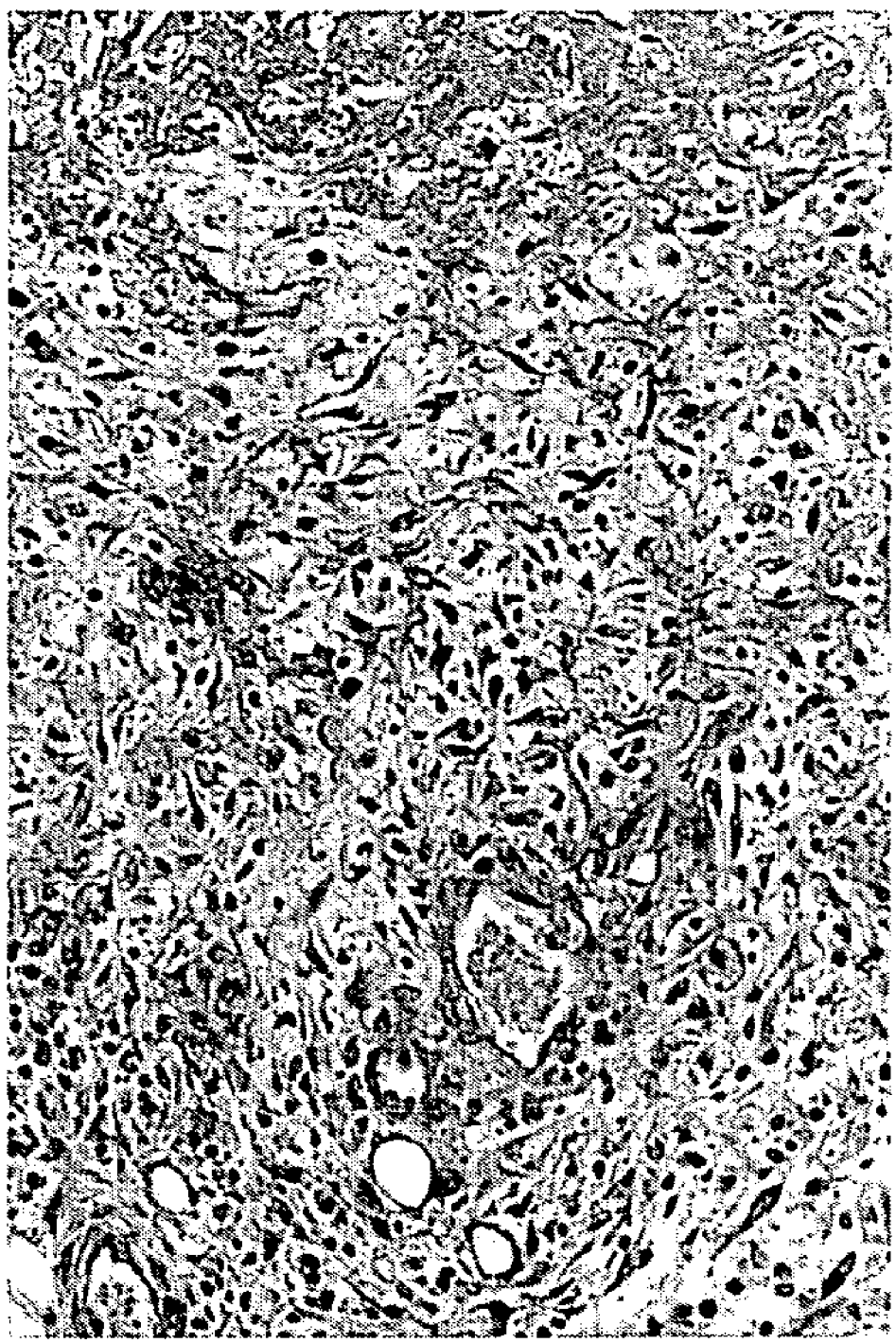
FIG. 1C is a photograph depicting TG activity as measured by the generation of isopeptide bonds in wounded tissue at the border with normal tissue. Isopeptide bonds appear brown in the figure.
Figure 1D:
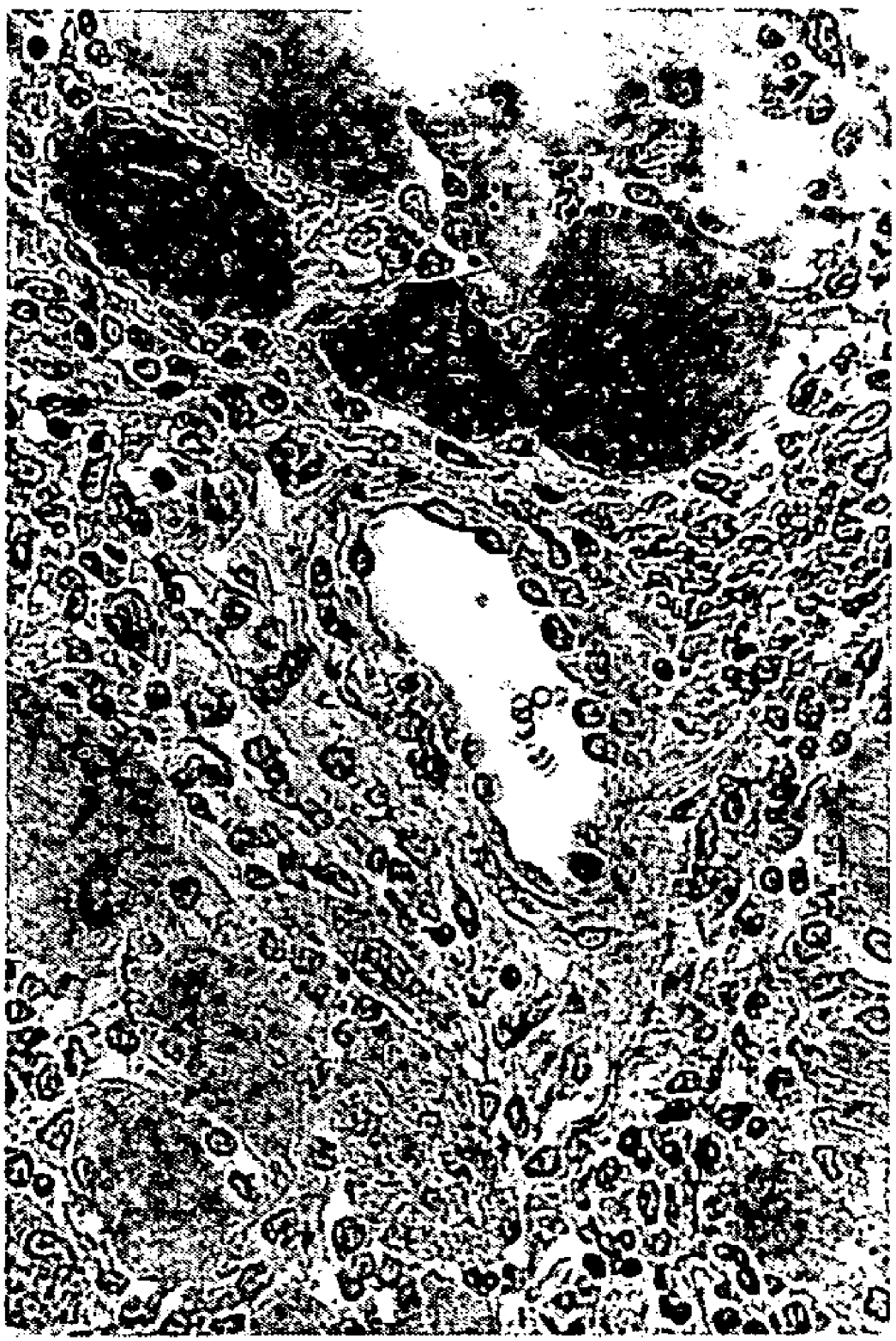
FIG. 1D is a photograph depicting TG activity as measured by the generation of isopeptide bonds in tumor tissue at the border with normal tissue. Isopeptide bonds appear brown in the figure.

Crosslink formation mediated by $FXIII_a$ can be monitored using the fluorescence-based TG crosslinking assays described above, which can be modified mutatis mutandis for use in determining $FXIII_a$ mediated crosslinking activity. Of course $FXIII_a$ will be substituted for TG in these assays. Other $FXIII_a$ and TG activity assays useful in the present invention will be apparent to those of skill in the art. See, e.g., Bowness et al., (1987) *J. Biol. Chem.* 262(3): 1022–24; Lorand & Campbell, (1971) *Anal. Biochem.* 44(1): 207–20. The described assays will be indicative of crosslink formation and, consequently, isopeptide bond formation, which is depicted in FIGS. 1C and 1D and indicated by the brown colored areas.

VI. Analysis of MR Properties of Candidate Contrast Enhancement Agents

After determining the biological relevance of a generated contrast enhancement agent, the agent's utility for MR-based applications should be evaluated. Thus, determination of the relaxivity profiles of candidate contrast enhancement agents is an aspect of the present invention.

Generally, when a chelator (e.g., DTPA) binds a paramagnetic metal ion, there is a reduction in relaxivity caused by shielding of the paramagnetic centers from water. One representative, but not exclusive, example involves gadolinium-DTPA wherein the complex has about one-half the relaxivity of free gadolinium ion. The chelator component of the contrast enhancement agents of the present invention employed in tumor and blood clot imaging applications act to improve the relaxivity of the paramagnetic metal ions by a cross relaxation mechanism.

For low molecular weight contrast enhancement agents, crosslinking of a contrast enhancement agent by TG or $fXIII_a$ to the ECM will increase the specific relaxivity of the agent by increasing the rotation time of the agent. Based on this observation, the contrast enhancement agent can be optimized so as to provide the highest sensitivity for the crosslinked product, and minimal signal enhancement for the free agent. Unrelated studies have shown that protein-(Gd-DTPA) conjugates exhibit 1.4–2.0-fold greater longitudinal relaxivities at 0.02 and 0.44 T than the relaxivity of free Gd-DTPA. See, e.g., Paajanen et al., (1990) *Magn. Reson. Med.* 13: 38–43.

The $T_1$ relaxivity of a candidate contrast enhancement agent in solution can be assessed using a 9.4 T NMR spectrometer by inversion recovery with 16 inversion times, and 10 different concentrations of the contrast material. Conditions useful for a $T_1$ relaxivity assessment include, but are not limited to, measurements of $T_1$ relaxivity in PBS-BSA solution, in a fibrin plug without crosslinking and in a fibrin plug with TG and, therefore, with crosslinking.

VII. In vivo Analysis of a Candidate Contrast Enhancement Agent

Following an initial in vitro characterization of a candidate contrast enhancement agent, the in vivo utility of a candidate contrast enhancement agent can be preliminarily determined. An in vivo assessment is valuable in generating a toxicity and physiological response profile for a candidate contrast enhancement agent, as well as providing a preliminary indication of the degree of enhancement achievable by a candidate agent. In order to serve as a contrast enhancement agent, a candidate contrast enhancement agent should behave like a tracer and not exhibit a significant degree of adverse effects, yet still contribute to highly detailed MR-generated images. Parameters that can be considered in a preliminary assessment of a candidate agent include, but are not limited to, body weight, wound healing, tumor growth rate, blood clot formation and general toxicity. Assessments of these parameters, where applicable, can be made using mouse, cat or dog models as desired and appropriate. Assays for general toxicity are known and suitable assays will be apparent. Examples of suitable parameters to monitor in general toxicity assays include body weight, blood chemistry and complete blood count ("CBC").

VII.A. In vivo Assays

A candidate contrast enhancement agent of the present invention can be applied to a variety of models and systems to generate high-definition images. High-definition images, however, are dependent on a number of variables. For example, one important consideration is the concentration of TG in a sample, and consequently the degree of TG activity in the sample. Another consideration is the degree to which a candidate contrast enhancement agent can be crosslinked by TG. Thus, it can be helpful to generate a preliminary assessment of the applicability of a candidate contrast enhancement agent to the system or model of interest. Using the preliminary assessment as a starting point, a system's variable parameters can be altered and optimized to arrive at the most advantageous conditions for MR imaging. Image optimization protocols described herein and known in the art can be applied to generate the highest possible quality MR image. A preliminary assessment determination can be made for any suitable biological model, with mouse, cat and dog models being particularly preferred for preliminary determinations, in anticipation of a human model.

VII.A.1. Wound Healing Assessment

In another method of optimizing imaging conditions, a candidate agent's potential can be assessed in a wound healing assay. In one wound healing assay, full thickness surgical incisions are created in a subject. A candidate contrast enhancement agent is then administered as described herein or by other known methods. The candidate agent is administered either to the blood stream of the subject or directly to the zone surrounding the wound. Wounds are monitored over time, which is a separately optimized variable, using magnetic resonance methods. It is known that TG is active in areas of wound healing and therefore, an effective candidate contrast enhancement agents will be found to accumulate at the site of an incision, where TG activity is high. Ineffective candidates will not be found in high quantities near the site of a wound. Additionally, TG activity can be identified and quantitated ex vivo using assays performed on prepared histological sections. In cases in which a candidate agent is localized to the area of a wound, MR parameters can be varied to create a highly detailed image of the wound site at different time points.

In another wound healing assay, a punch biopsy is performed to create a wound, rather than surgical incisions. Subsequently, a candidate contrast enhancement agent is administered to the subject. Wound healing and TG crosslinking activity is monitored as described for surgical incisions.

VII.A.2. Tumor Models

Yet another in vivo assay of the utility of a candidate contrast enhancement agent's potential involves tumor models. In practice, the contrast enhancement agents of the present invention can be used to image tumor tissue, particularly the TG-containing boundary between tumor and normal tissue. Thus, an assay involving tumor tissue will be of great value in determining the potential of a candidate agent for the in vivo imaging of tumor tissue.

Subjects expressing subcutaneous tumors can be studied using cells exhibiting variable expression of TG. These cells can be generated or isolated, and the assessment can be made in vivo or in vitro. Orthotopic implants can be of particular use as metastasis models for the use of the present invention in tumor models. The use of orthotopic implants involves implanting tumor cells into anatomically relevant organs. Since it has recently been found that implanted tumor cells can serve as a model of the clinical pathophysiology of growth, invasion and metastasis, orthotopic implantation has become an attractive method of modeling tumor metastasis and can be used in the context of the present invention.

In the context of the present invention, standard methods are available for preparing orthotopic implants; that is, implanting tumor tissue into organ tissue. Following such an implantation, the tumor can be treated with candidate molecules prepared in accordance with the present invention. Those candidate molecules that are recognized and crosslinked by TG will form structures amenable to imaging, due to the presence of the contrast enhancement agent in the crosslinked structured, and the high degree of TG activity at the borders of a tumor. Those candidate molecules that are not recognized will not appear when MR images are generated. Using this general method, it is possible to determine the potential for a candidate molecule to effectively assist in monitoring tumor size and regression.

VII.A.3. Blood Clot Imaging Models

In a further in vivo assay of the utility of a candidate contrast enhancement agent's potential a blood clotting model is employed. In practice, the contrast enhancement agents of the present invention can be used to image blood clots.

In one particularly useful blood clot model, a suitable endotoxin is administered to a subject. Endotoxins have the effect of activating the clotting pathway. Thus, following administration of an endotoxin, a candidate contrast enhancement agent of the present invention is administered to the subject. The endotoxin will have the effect of inducing clotting, and the candidate contrast enhancement agent will, if recognized and subsequently crosslinked by $fXIII_a$, be incorporated into a formed blood clot. Crosslinked contrast enhancement agents will permit images of the agent-containing blood clot to be obtained. Similarly, the dissolution of a blood clot within which a contrast enhancement agent of the present invention is contained can be imaged. The dissolution can be monitored as a function of time as the clot is degraded.

VII.A.4. Angiogenesis

The ability to monitor angiogenesis in vivo is an important aspect of the present invention. Angiogenic activity will be present in a variety of tissues and can be correlated with elevated TG activity. Thus, contrast enhancement agents that are recognized and crosslinked by TG can be used to monitor angiogenic activity in a given tissue or structure.

Elevated angiogenesic levels will be found in tumor tissue and other tissues existing in a diseased state. These tissues will also exhibit elevated TG activity levels. Angiogenesis can be monitored by generating a time course of images and evaluating TG activity as a function of time. The methods described hereinabove for the administration of a candidate contrast enhancement agent are equally applicable to the study of angiogenesis.

Briefly, the utility of a candidate contrast enhancement agent can be determined by monitoring TG activity in a localized region. A candidate agent is incubated with angiogenic tissue or tissue suspected of angiogenic activity. Subsequently, MR images of the tissue are obtained and evaluated for the presence of the agent. Candidate agents that are recognized and crosslinked by TG will appear in obtained images. Those agents that are not recognized by TG will not be crosslinked and will not appear in images. Those agents that are crosslinked by TG will be useful for obtaining images of tissue undergoing angiogenesis.

VIII. In vivo Mapping of TG Activity by MRI

Mapping TG activity in wounded tissue, tumor tissue boundaries, (depicted in FIGS. 1C and 1D, respectively), blood clots, wound healing structures angiogenic tissue and other subject structures involves at least two steps. First, before any contrast enhancement agent is added to the system, a "pre-contrast" $T_1$ map of the subject structure is generated. The pre-contrast map is constructed from inversion recovery Rapid Acquisition with Refocused Echoes ("RARE") images from eight "time from inversion" ("TI") time points. The pre-contrast map is essentially an unmodified form of the basic MRI experiment. Next, a TG-recognized contrast enhancement agent is presented to the subject structure using methods disclosed in the present invention and another map is generated, a "post contrast" map. The post contrast map will show the incorporation of contrast enhancement agent, which will be recognized and bound by TG. To create the post-contrast map, images are taken at various predetermined acquisition time points. The only restrictions on the selection of the number and time of acquisition points, both of which can be predetermined during the design of an MRI experiment to optimize or focus on desired parameter or effect, is the longevity of a contrast enhancement agent's effective lifetime and considerations of the subject structure's maintained integrity.

After presenting a contrast enhancement agent to a subject structure, at least two TI values are obtained for each time point arising within 30 minutes of the presentation of the contrast enhancement agent to the subject structure. At least eight TI values are taken for time points greater than 30 minutes after the introduction of the contrast enhancement agent. The pre- and post-contrast maps are subsequently compared. The comparison of the two maps provides an indication of TG activity in the subject structure and the localization, if any, of the TG activity. Alternatively, the pre-contrast map can be mathematically subtracted from the post-contrast map using standard MRI software to generate a difference map. The resulting difference map can exclusively highlight regions where TG-crosslinking of a presented contrast enhancement agent is occurring.

IX. Applications for TG and $fXIII_a$-Recognized Contrast Enhancement Agents

Generally, a contrast enhancement agent of the present invention can be applied to any system known or predicted to exhibit TG or $fXIII_a$ activity. Representative systems include, but are not limited to, tumor tissue, angiogenic tissue and blood clots. The contrast enhancement agents of the present invention are particularly useful for monitoring a decrease or increase in tumor size and for monitoring the formation and dissolution of blood clots.

As described herein, TG expression and activity is high at the border of tumors (FIGS. 1B and 1D, respectively). Thus, a contrast enhancement agent of the present invention can be used, in conjunction with MR methods, to obtain clear images of the boundary between tumor and normal tissue and, consequently, the morphology of a tumor. Additional images obtained over time can be analyzed for physiological responses to tumor treatment. Additionally, a contrast enhancement agent of the present invention can be used as a diagnostic tool to ascertain the presence of a tumor. Early detection of tumors can provide medical professionals with a wider range of treatment alternatives than are available at a stage when a tumor is further developed.

It has been shown that TG is expressed very early during wound healing and stains intensely the border between normal and wounded tissue (Haroon et al., (1999a) *FASEB J.* 13:1787–95). In human and murine breast tumors, it has been observed that TG associated with the neovasculature and the ECM at the interface between tumor and normal host tissue (Haroon et al., (1999b) *Lab. Invest.* 79:1679–86; Hettasch et al., (1996) *Lab. Invest.* 75:637–45). Isopeptides at these interfaces have also been detected, indicating that TG was active (Haroon et al., (1999a) *FASEB J.* 13:1787–95; Haroon et al, (1999b) *Lab. Invest.* 79:1679–86). Assessment of the activity of the enzyme by probing the tissues with an antibody to isopeptide bonds indicated that the maximum intensity of the isopeptide bonds occurred in the border regions between normal and inflamed or tumor tissue. This result indicates that TG is expressed as part of a host response to injury and tumor growth and is actively crosslinking in that zone. Thus, a contrast enhancement agent of the present invention will be useful to monitor wound healing structures.

Additionally, a contrast enhancement agent of the present invention can be used to monitor angiogenesis in a subject. Angiogenic tissue is known to exhibit high TG activity. If the detection of localized TG activity, and consequently angiogenic activity, is performed over time, angiogenic activity can be compared at various time points. Localized angiogenic activity, indicated by high TG activity, identified by a contrast agent of the present invention can be indicative of tumor formation and can alert medical professionals to an emergent condition. Again, early detection of such a condition gives medical professionals time to perform additional tests and presents a wider range of treatment options for an afflicted subject.

Further, a contrast agent of the present invention can be used to monitor blood clot formation. One advantage of the contrast enhancement agents of the present invention is that they permit real-time imaging of blood clot formation. This application finds particular utility for subjects recovering from heart attacks where repeated clot formation can be life-threatening.

IX.A. Imaging Tumor Boundary Regions

TG concentration and activity is high at the boundaries of tumors. Haroon et al., (1999b) *Lab. Invest.* 79: 1679–86; Hettasch et al., (1996) *Lab. Invest.* 75: 63745. This observation permits imaging of these areas using contrast enhancement agents specifically recognized by TG. A contrast enhancement agent of the present invention comprises a protein or peptide component known to be crosslinked by TG, coupled to an MR detectable component. When the agent is presented to TG, the agent is crosslinked and localized to the area of high TG concentration. Standard MR equipment and techniques can be used to image areas of TG localization.

A time-dependent map of an area of high TG localization can be analyzed for changes in TG activity. Observed changes can correlate with tumor mass. Thus, in one aspect of the present invention, a contrast enhancement agent of the present invention can be used to determine the effect of a therapeutic treatment regime. In this aspect, a therapeutic tumor treatment agent is administered to a subject. The effect of the therapeutic on the growth of the tumor can be determined by monitoring the mass of the tumor. Effective therapeutics will reduce the mass of the tumor, while ineffective therapeutics will have little or no effect on tumor mass. Changes in tumor mass can be ascertained by tracking changes in tumor mass over time, using a contrast enhancement agent of the present invention.

IX.B. Real-Time Imaging of Blood Clot Formation

The contrast enhancement agents of the present invention are useful for generating real-time images of blood clot formation. Blood clots are stabilized by a sister enzyme of TG, $fXIII_a$. Factor $XIII_a$ is activated by thrombin as the clot is formed. Specifically, $fXIII_a$ catalyzes linear crosslinking between the γ chains of fibrin to form γ dimers. Factor $XIII_a$ then stabilizes the clot; without $fXIII_a$, the clot would rapidly degrade. Substrates of $fXIII_a$ comprise the same amino acid sequence found in peptides and proteins recognized by TG, namely SEQ ID NO: 2. Thus, substrates recognized by TG are also recognized by fXIII$_a$.

Contrast enhancement agents of the present invention are substrates of fXIII$_a$ and are useful for imaging blood clots. In practice, a contrast enhancement agent of the present invention can be introduced into the blood stream of a subject, or can be locally injected into tissue. As thrombin activates fXIII$_a$ in the process of forming a blood clot, a contrast enhancement agent of the present invention present in the local area of the developing clot will be incorporated into the growing clot. As the clot increases in mass, more contrast enhancement agent is incorporated into the clot. The incorporated agent can be imaged using MR techniques and equipment generally known in the art, and images can be acquired during clot formation and after the clot is formed for as long as the clot and the agent maintain their integrities. Thus, a contrast enhancement agent of the present invention can be used to create images of blood clot formation. Although known angiography and ultrasound can provide images useful for observing blood clot formation, neither of these techniques can provide the degree of detail, localization and real-time imaging ability facilitated by the contrast enhancement agents of the present invention.

IX.C. Imaging Wound Healing Zones

It is known that TG is expressed in the very early stages of wound healing, and is strongly, but not exclusively, localized to the border between normal and wounded tissue (Haroon et al., (1999a) *FASEB J.* 13:1787–95). In light of the TG expression profile in tumor cells and wound tissue, TG is expressed as part of a host response to injury and tumor growth and is actively catalyzing crosslinking in these zones.

In areas where TG activity is high, such as in areas of wound healing, contrast enhancement agents comprising a recognized peptide or protein component will be recognized and bound by TG. The contrast enhancement agents of the present invention are bound by TG and will, therefore, be very concentrated at the site of the wound healing. The contrast enhancement agent permits imaging of the TG-containing tissue in regions of wound healing.

IX.D. TG and fXIII$_a$-Recognized Contrast Enhancement Agents as Research Tools

The basic biology of tumor progression is not comprehensively understood. The contrast enhancement agents of the present invention can help elucidate the basic biology of tumors. One theory of tumor progression holds that as tumors progress, they invade into the neighboring tissue and occupy the previous tumor-host boundary. Another theory holds that as a tumor regresses, the tumor-host boundary is replaced by normal host cells, with concomitant degradation of the ECM. Both of these theories, as well as other aspects of tumor biology, can be investigated using a contrast enhancement agent of the present invention.

By way of example, if the first hypothesis of tumor progression is correct, an amount of contrast enhancement agent introduced to a tumor tissue will be bound and localized to the tumor boundary and will be found within the tumor mass as the tumor progresses. If this hypothesis is not correct, one possibility is that the tumor will expand by inflating, rather than invading, and the contrast will remain at the boundary of the larger tumor.

If the second hypothesis is proven to be correct, namely that upon tumor regression the tumor-host boundary is replaced by normal host cells, an amount of contrast enhancement agent introduced to tumor tissue will be bound and localized to the tumor boundary will be the first to disappear with tumor regression. If this hypothesis is not correct, a possible result is that the tumor will regress by loss of volume from the inner tumor mass, and the contrast will remain at the boundary of the shrinking tumor.

Regardless of which hypothesis is proven to be correct, the contrast enhancement agents of the present invention will be a valuable research tool for those researchers in many fields, particularly in the field of tumor biology and pharmaceutical research and development. The ability to image tumor tissue and other areas of high-TG activity can provide researchers with a tool to study the morphology and progression of a tumor in a way unknown prior to disclosure of the present invention.

Additionally, the contrast enhancement agents of the present invention can aid in the development of anti-tumor therapeutics. For example, the ability to image tumor boundaries will be useful to qualitatively and quantitatively measure the effect of a candidate therapeutic on a tumor's progression or regression.

Finally, the contrast enhancement agents of the present invention will be useful as a tool for studying blood clot formation. The effect of candidate anti-coagulants and clot-inducing compounds on clot formation can be monitored using a contrast enhancement agent of the present invention. Using the contrast enhancement agents of the present invention as a tool, researchers can quickly determine if a compound, e.g. a compound suspected to exhibit coagulant or anti-coagulant activity, effectively inhibits blood clot formation. A particular advantage in this regard is the ability to monitor the effect of a compound on clot formation in real time.

X. Evaluation of Experimental Parameters

A number of experimental parameters can be monitored when contrast enhancement agents are introduced into a subject. The following section details three determinations that can be made, although experimental and subject requirements can dictate further parameters. Such requirements will be apparent as an experiment proceeds.

X.A. Determining the Concentration of Unbound Contrast Enhancement Agent

The contrast enhancement agents of the present invention can be systemically administered to a subject by injection using a variety of methods, including those disclosed herein. This route of administration is useful for imaging the boundary between tumor and normal tissue, and finds particular utility as a method of imaging blood clot formation. In these applications, as well as in the design of a candidate contrast enhancement agent, it is helpful to determine the amount of contrast enhancement agent bound by TG and fXIII$_a$ in a subject, and consequently the amount of agent that remains unbound in a subject. Unbound agent will, for a time, be disposed in the subject's blood stream.

The concentration of unbound contrast material in the blood stream of a subject at a given time can be determined by obtaining axial MR images of large blood vessels. Unbound agent will appear as regions of high contrast in MR images. The contrast density of the images can be mathematically correlated with the amount of unbound agent in the subject's blood stream by applying densitometric methods. Generation of a calibration curve can assist in this determination.

Concentration determinations made based on axial images can be verified by examining blood samples extracted at later time points. Unbound contrast enhancement agent can be isolated from a blood sample using standard centrifugation and chromatographic methods. The concentration of isolated contrast enhancement agent can be determined using spectroscopic or MR-based techniques.

X.B. Validation of MR-generated Results

MR-generated pharmacokinetic and TG mapping results can be validated spectroscopically against energy emission from a doubly-labeled agent. A doubly-labeled agent can comprise a contrast enhancement agent of the present invention which has been associated with a second label capable of emitting energy under certain conditions. The contrast enhancement agent component of a doubly-labeled agent can be conveniently prepared as described herein. Methods for the association of a label with another compound are well known in the art. Preferably, the second label will be a fluorescent label and the energy emission will be fluorescent emission, although other energy emitting labels can be used and can be determined in the course of experimental design.

A doubly-labeled agent of the present invention can comprise a contrast enhancement agent component and a fluorescence-emitting component. A doubly-labeled agent thus enables two forms of agent detection, MR-based detection and spectroscopic detection. The two forms of detection can be used to independently validate observed pharmacokinetic results.

Validation of pharmacokinetic results can be conveniently performed using a doubly-labeled contrast enhancement agent in vivo or in vitro. For example, the pharmacokinetic properties of a doubly-labeled agent can be studied in vivo using both MR and spectroscopic techniques. Alternatively, a doubly-labeled agent can be isolated either as unbound agent or complexed with TG or fXIIIa and studied in vitro using both MR-based and spectroscopic techniques. Behavior documented using MR-based detection can be further documented using spectroscopic detection, and conversely, behavior documented using spectroscopic detection can be further documented using MR-based detection. Comparable results from both studies can provide verification of the overall experiment.

X.C. Selection and Preparation of Experimental Controls

When determining the kinetic parameters associated with the TG and $fXIII_a$ crosslinking event (and thus in vivo mapping of TG activity), it is necessary to include experimental control samples. Appropriate controls will include samples known to recognized by TG and $fXIII_a$, and samples known to be unrecognized by TG and $fXIII_a$. A key to the contrast enhancement agents of the present invention is their ability to be bound by TG and $fXIII_a$, which is imparted by the peptide or protein component of the agent. Thus, a negative control can comprise a protein or peptide sequence not recognized by TG or $fXIII_a$.

The sequence shown in SEQ ID NO: 3, in which the residue at the second position of the peptide is known to be unrecognized by TG and $fXIII_a$, and therefore can form the basis of a suitable negative control. By complexing a peptide of SEQ ID NO: 3 with a contrast enhancement agent of the present invention, a negative control can be generated.

Generation of a positive control sample can be pursued in a similar fashion, with the protein component comprising a protein or peptide known to be recognized by TG. Generated controls will serve to validate observed crosslinking or absence of crosslinking catalyzed by TG or $fXIII_a$ and involving a candidate contrast enhancement agent.

XI. Kit for Contrast Enhancement in MR Imaging

In another embodiment, the present invention provides a kit comprising a two-vial system, used for preparing a contrast enhancement agent useful in in vivo MR imaging. The kit comprises a first vial comprising lyophilized contrast enhancement agent, and a second vial containing a liquid diluent. The first vial can optionally comprise other components, for example a drying protectant. The liquid diluent of the second vial will be a pharmaceutically acceptable diluent, such as sterile water, for example. Alternatively, the diluent can be selected from any of a range of suitable buffers, all of which provide the added advantage of providing a stable pH. Buffers suitable for use in the present invention include phosphate buffers, borate buffers, Tris buffer and HEPES buffer, all of which can further comprise a sterile saline solution. Most preferably, the liquid diluent is phosphate buffer saline.

In use, the contrast enhancement agent components of the kit are provided in a single sterile vial in lyophilized form. The lyophilized contrast enhancement agent is reconstituted with a pharmaceutically acceptable diluent, which is provided in the second vial. Other suitable reagents can optionally be provided, for example buffer.

The kit of the present invention has provides a stable formulation of a contrast enhancement agent, which has a long shelf life when stored at 4° C. A fresh stable solution of a contrast enhancement agent suitable for use can be prepared at any desired time by mixing the contents of the second vial with the contents of the first vial. The resulting solution can then be used immediately and can be delivered directly to the sample or subject.

In preparing the kits of the present invention, the ultimate delivery system prepared from the kit must be sterile, non-antigenic and free of infectious agents, such as bacteria. Therefore, the kit must be prepared under aseptic conditions or the kit and ingredients must be sterilizable. Packaging materials, such as glass and rubber can be sterilized by steam. Liquid components can be sterile filtered through 0.22 micron filters. The prepared contrast enhancement agent can itself be filtered to further assure sterility.

XII. Functional Equivalency

It will be understood by those of skill in the art that amino acid sequences can include additional residues, such as additional N- or C-terminal amino acids (e.g., a poly-lysine tail), and yet still be essentially as set forth in the sequence disclosed herein, so long as the sequence retains biological activity.

XII.A. Biological Equivalents

The present invention envisions and includes biological equivalents of the peptides and proteins of the present invention. The term "biological equivalent" refers to peptides and proteins having amino acid sequences which are substantially identical to the amino acid sequence of a TG- or $fXIII_a$-recognized protein or peptide of the present invention and which are capable of exerting a biological effect in that they are capable of crosslinking to TG and/or $fXIII_a$, or cross-reacting with antibodies raised against a peptide of the present invention.

Certain amino acids can be substituted for other amino acids in a protein or peptide structure without appreciable loss of interactive capacity with other proteins, for example, TG or $fXIII_a$. Since it is the interactive capacity and nature of a protein or peptide that defines that protein or peptide's biological functional activity, certain amino acid sequence substitutions can be made in an amino acid sequence (or the nucleic acid sequence encoding it) to obtain a protein or peptide with the same, enhanced, or antagonistic properties. Such properties can be achieved by interaction with the normal targets of the peptide, but this need not be the case, and the biological activity of the invention is not limited to a particular mechanism of action. It is thus in accordance with the present invention that various changes can be made in the amino acid sequence of a protein or peptide of the present invention without appreciable loss of biological utility or activity.

Biologically equivalent proteins and peptides, as used herein, are proteins and peptides in which certain, but not most or all, of the amino acids can be substituted. Thus, when referring to the sequence examples presented in SEQ ID NOs: 1–3, applicants envision substitution of biologically equivalent amino acids, as described herein, into the sequence example of SEQ ID NOs: 1–3. Thus, applicants are in possession of amino acid sequences which include such substitutions but which are not set forth herein in their entirety for convenience.

Alternatively, functionally equivalent peptides can be created via the application of recombinant DNA technology, in which changes in the protein or peptide can be engineered, based on considerations of the properties of the amino acids being exchanged, e.g. substitution of lie for Leu. Changes designed by man can be introduced through the application of site-directed mutagenesis techniques or though peptide synthesis methods well known in the art.

Amino acid substitutions, such as those which might be employed in modifying a protein or peptide of the present invention are generally, but not necessarily, based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art. It is implicit in the above discussion, however, that one of skill in the art can appreciate that a radical, rather than a conservative substitution is warranted in a given situation. Non-conservative substitutions in the proteins and peptides of the present invention are, therefore, also an aspect of the present invention.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, (1982), *J. Mol. Biol.* 157: 105–32, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a peptide, as governed by the hydrophilicity of its adjacent amino acids, correlates with its immunogenicity and antigenicity, i.e. with a biological property of the peptide. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent proteins and peptides arising from amino acid changes, it will be appreciated that these changes can be effected by alteration of a sequence of DNA encoding a peptide or protein, taking into consideration also that the genetic code is degenerate and that two or more codons can code for the same amino acid.

Thus, it will also be understood that this invention is not limited to the particular amino acid sequences of SEQ ID NOs: 1–3. Recombinant vectors and isolated DNA segments employed in generating the peptides and proteins of the present invention can variously include an engineered peptide-encoding region itself, include coding regions bearing selected alterations or modifications in the basic coding region, or include larger peptides which nevertheless comprise a peptide of SEQ ID NOs: 1–3. Biological activity of an engineered peptide can be determined, for example, by a variety of TG-recognition assays including those disclosed herein.

The invention further encompasses fusion peptides wherein an engineered coding region of the present invention is aligned within the same expression unit with other proteins or peptides having desired functions, such as for purification or immunodetection purposes.

REFERENCES

The references listed below as well as all references cited in the specification are incorporated herein by reference to the extent that they supplement, explain, provide a background for or teach methodology, techniques and/or compositions employed herein.

Achyuthan, (1994) *Anal. Biochem.* 219:43–48
Aeschlimann & Paulsson, (1991) *J. Biol. Chem.* 266: 15308–17
Aeschlimann & Paulsson, (1994) *Thromb. Haemostasis* 71: 402–15
Aeschlimann et al., (1995) *J. Cell Biol.* 129: 881–92
Baumert & Fasold, (1989) *Methods Enzymol.* 172: 584, Academic Press, New York
Belliveau et al., (1991) *Science* 254: 719
Bowness et al., (1987) *J. Biol. Chem.* 262(3): 1022–24

Chen & Doolittle, (1970) *Proc. Natl. Acad. Sci. U.S.A.* 66: 472–79
Chung et al., (1974) *J. Biol. Chem.* 249: 940–950
Clark & Coker, (1998) *Int. J. Biochem. Cell Biol.* 30: 293–98
Dvorak et al., (1987) *Lab. Invest.* 57(6): 673–86
Everse & Stolzenbach, (1971) *Methods Enzymol.*, 22: 33–39, Academic Press, New York
Fields & Noble, (1990) *Int. J. Pept. Prot. Res.* 35:161–214
Folk & Finlayson, (1977) *Adv. Protein Chem.* 31: 1–133
Folkman, (1995) *New Engl. J. Med.* 28:333(26), 1757–63
Flosdorf, (1949) *Freeze-Drying*, Rheinhold Pub. Corp., New York
Gentile et al., (1991) *J. Biol. Chem.* 266: 478–83
Gentile et al., (1992) *J. Cell Biol.* 119: 463–74
George et al., (1990) *J. Biol. Chem.* 265:11098–104
Greenberg & Shuman, (1982) *J. Biol. Chem.* 257: 6096–6101
Greenberg et al., (1987) *Blood* 70: 702–9
Greenberg et al., (1991) *FASEB J.* 5: 3071–77
Haroon et al., (1999a) *FASEB J.* 13: 1787–95
Haroon et al., (1999b) *Lab. Invest.* 79: 1679–86
Hettasch et al., (1996) *Lab. Invest.* 75: 637–45
Hohenadl et al., (1995) *J. Biol. Chem.* 270:23415–20
Ichinose et al., (1986a) *Biochem.* 25: 4633–38
Ichinose et al., (1986b) *Biochem.* 25: 6900–906
Ikura et al., (1994) *Biosci. Biotechnol. Biochem.* 58: 1540–41
Jensen et al., (1993) *Eur. J Biochem.* 214: 141–46
Kean & Smith, (1986) *Magnetic Resonance Imaging: Principles and Applications*, Williams and Wilkins, Baltimore, Md.
Kojima et al., (1993) *J. Cell Biol.* 121: 439–48
Kuncio et al., (1998) *Am. J. Physiol.* 274: G240–45
Kyte & Doolittle, (1982), *J. Mol. Biol.* 157: 105–132
Lorand & Campbell, (1971) *Anal. Biochem.* 44(1): 207–20
Lorand & Conrad, (1984) *Mol. Cell. Biochem.* 58: 9–35
Lorand et al., (1972) *Anal. Biochem.* 50: 623
Lorand et al., (1974) *Biochem. Biophys. Res. Comm.* 56: 914–922
Lorand et al., (1980) *Prog. Hemost. Throm.* 5: 245–290
Meyer et al., (1990) *Invest. Radiol.* 25: S53
Mosher & Chad, (1979) *J. Clin. Invest.* 64: 781–787
Mosher, (1975) *J. Biol. Chem.* 250: 6614–6621
Nara et al., (1994) *J. Biochem.* (Tokyo) 115: 441–48
Ogan et al., (1987) *Invest. Radiol.* 22: 665–71
Paajanen et al., (1990) *Magn. Reson. Med.* 13(1): 38–43
Pepper, (1997) *Cytokine Growth Factor Rev.* 8: 21–43
Pisano et al., (1972) *Ann. N. Y. Acad. Sci.* 202: 98–113
Runge et al., (1991) *Magn, Reson. Imaging* 3: 85
Russell et al., (1989) *Am. J. Roentgenol.* 152: 813
Sakata & Aoki, (1980) *J. Clin. Invest* 65: 290–97
Sakiyama et al., (1999) *FASEB* 13:2214–24
Sane et al., (1988) *Biochem. Biophys. Res. Commun.* 157: 115–20
Slaughter et al., (1992) *Anal. Biochem.* 205: 166–71
Weinman et al., (1984) *Am. J Radiol.* 142: 619
Yee et al., (1994) *Proc. Natl. Acad. Sci. U.S.A.* 91: 7296–7300
Yee et al., (1996) *Sem. Thromb. Haemostasis* 22: 377–84
U.S. Pat. No. 4,554,101
U.S. Pat. No. 4,797,369
U.S. Pat. No. 5,710,174
U.S. Pat. No. 5,155,215
U.S. Pat. No. 5,925,987
U.S. Pat. No. 6,022,747
U.S. Pat. No. 4,885,363
U.S. Pat. No. 5,087,440
U.S. Pat. No. 5,188,816
U.S. Pat. No. 5,219,553
U.S. Pat. No. 5,262,532
U.S. Pat. No. 5,358,704

It will be understood that various details of the invention can be changed without departing from the scope of the invention. Furthermore, the foregoing description is for the purpose of illustration only, and not for the purpose of limitation—the invention being defined by the claims.

What is claimed is:

1. A method for preparing a contrast enhancement agent, the method comprising:
   (a) preparing a contrast enhancement agent wherein the agent is in lyophilized form and comprises at least one peptide comprising the sequence NXEQVSP (SEQ ID NO: 1), and further wherein X is an amino acid selected from the group consisting of alanine, arginine, asparagine, aspartic acid, cysteine, glutamic acid, glycine, histidine, isoleucine, leucine, lysine, methionine, phenylalanine, proline, serine, threonine, tryptophan, tyrosine and valine; and
   (b) admixing the contrast enhancement agent with an aqueous pharmaceutically acceptable diluent, whereby a contrast enhancement agent is prepared.

2. The method of claim 1, wherein the aqueous pharmaceutically acceptable diluent is phosphate buffer saline.

3. A method of non-invasively generating a visible image of a biological sample, the method comprising:
   (a) providing a contrast enhancement agent comprising:
      i) at least one peptide comprising the sequence NXEQVSP (SEQ ID NO: 1), wherein X is an amino acid selected from the group consisting of alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine;
      ii) at least one paramagnetic metal ion; and
      (iii) at least one chelator;
   (b) introducing the contrast enhancement agent to a biological sample; and
   (c) scanning the biological sample using magnetic resonance imaging, whereby a visible image of a biological sample is non-invasively generated.

4. The method of claim 3, wherein the paramagnetic metal ion is selected from the group consisting of transition elements and inner transition elements.

5. The method of claim 4, wherein the paramagnetic metal ion is selected from the group consisting of Gd(III), Mn(II), Cu(II), Cr(III), Fe(II), Fe(III), Co(II), Er(II), Ni(II), Eu(III) and Dy(III).

6. The method of claim 3, wherein the chelator is selected from the group consisting of DTPA, substituted DTPA, DOTA, substituted DOTA, EDTA, substituted EDTA, CDTA and substituted CDTA.

7. The method of claim 3, wherein the imaging agent is disposed in a pharmaceutically acceptable diluent.

8. The method of claim 3, wherein the biological sample is disposed in a subject.

9. The method of claim 8, wherein the subject is a mammal.

10. The method of claim 9, wherein the mammal is a human.

11. The method of claim 9, wherein the mammal is selected from the group consisting of mouse, cat and dog.

12. The method of claim 8, wherein the biological sample is tumor tissue.

13. The method of claim 8, wherein the biological sample is blood.

14. The method of claim 8, wherein the biological sample is a blood clot.

15. The method of claim 8, wherein the biological sample is tissue undergoing angiogenesis.

16. The method of claim 8, wherein the biological sample is wounded tissue.

* * * * *